US011040186B2

(12) United States Patent
Burkholz et al.

(10) Patent No.: US 11,040,186 B2
(45) Date of Patent: Jun. 22, 2021

(54) PINCH CLAMP DEVICE

(71) Applicant: Becton, Dickinson and Company, Franklin Lakes, NJ (US)

(72) Inventors: Jonathan Karl Burkholz, Salt Lake City, UT (US); Bart D. Peterson, Farmington, UT (US); Bin Wang, Sandy, UT (US); Marty L. Stout, South Jordan, UT (US); Olivia Hu, Shanghai (CN); Weston F. Harding, Lehi, UT (US); Ralph L. Sonderegger, Farmington, UT (US); Kelvin Chai, Shanghai (CN); Lionel Wang, Jiangsu (CN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 257 days.

(21) Appl. No.: 15/286,248

(22) Filed: Oct. 5, 2016

(65) Prior Publication Data
US 2017/0120040 A1 May 4, 2017

Related U.S. Application Data

(60) Provisional application No. 62/247,615, filed on Oct. 28, 2015, provisional application No. 62/296,372, filed on Feb. 17, 2016.

(51) Int. Cl.
*A61M 39/28* (2006.01)
(52) U.S. Cl.
CPC ........ *A61M 39/288* (2013.01); *A61M 39/284* (2013.01)
(58) Field of Classification Search
CPC .. A61M 39/284; A61M 39/28; A61M 39/281; A61M 39/283; A61M 5/1414;
(Continued)

(56) References Cited

U.S. PATENT DOCUMENTS 3,344,966 A * 10/1967 Schaefer ................ A47G 25/48
223/96
3,698,681 A 10/1972 Lacey
(Continued)

FOREIGN PATENT DOCUMENTS

DE 102005004863 8/2006
EP 1555007 7/2005
(Continued)

OTHER PUBLICATIONS

"Coating". Macmillan Dictionary. <https://www.macmillandictionary.com/us/dictionary/american/coating> Accessed Mar. 5, 2019 (Year: 2019).*

*Primary Examiner* — Scott J Medway
(74) *Attorney, Agent, or Firm* — Kirton & Mcconkie; Craig Metcalf; Kevin Stinger

(57) ABSTRACT

Pinch-style clamps can be designed for use in clamping or occluding plastic tubing, such as intravenous tubing. These pinch clamps can include a soft, polymer material applied to various surfaces of the pinch clamp to prevent abrasion or irritation to the patient, increase friction between the pinch clamp and the user operating said pinch clamp, increase friction between engaged surfaces of the pinch clamp to prevent premature or unintended disengagement of the clamp, or increase friction between the outer surfaces of the tubing and the clamping surfaces of the clamp. Various features or components can be employed to prevent lateral disengagement of the pinch clamp. A pinch clamp may also be configured with rounded outer edges to enhance patient comfort.

20 Claims, 20 Drawing Sheets

(58) Field of Classification Search
CPC ......... A61M 5/16813; A61M 2025/024; F16L 21/007; F16K 7/063; F16K 7/066; Y10T 24/44752; Y10T 24/14; Y10T 24/3936; A61B 17/122; A61B 2017/00858

See application file for complete search history.

(56) References Cited

U.S. PATENT DOCUMENTS

| | | | | |
|---|---|---|---|---|
| 3,847,370 A * | 11/1974 | Engelsher | ........... | A61M 1/0078 222/214 |
| 3,924,307 A * | 12/1975 | Tate | ...................... | A47G 1/0638 24/543 |
| 4,053,135 A | 10/1977 | Salfaris | | |
| 4,097,020 A * | 6/1978 | Sussman | ................... | B05B 1/30 239/530 |
| 4,115,182 A * | 9/1978 | Wildmoser | ......... | B29C 65/7433 156/515 |
| 4,235,412 A | 11/1980 | Rath et al. | | |
| 4,346,869 A | 8/1982 | MacNeil | | |
| 4,429,852 A * | 2/1984 | Tersteegen | .......... | A61M 39/284 24/543 |
| 4,589,626 A * | 5/1986 | Kurtz | .................. | A61M 39/288 251/10 |
| 4,676,476 A | 6/1987 | Herrli | | |
| 4,854,766 A * | 8/1989 | Hein | .................. | B60G 21/0551 403/224 |
| 4,892,276 A * | 1/1990 | Alessio | ................. | F16L 3/1008 248/74.1 |
| 5,292,312 A * | 3/1994 | Delk | ..................... | A61M 25/02 128/DIG. 26 |
| 5,318,546 A | 6/1994 | Bierman | | |
| 5,395,344 A * | 3/1995 | Beisang, III | .......... | A61M 25/02 128/DIG. 26 |
| 5,842,932 A * | 12/1998 | Goddard | ............ | A63B 69/3685 473/240 |
| 5,865,813 A | 2/1999 | DeKalb et al. | | |
| 5,989,174 A * | 11/1999 | Patrizio | ................. | B31F 1/0009 493/413 |
| 6,079,328 A * | 6/2000 | Beck | ....................... | B41F 13/02 101/216 |
| 6,095,479 A * | 8/2000 | Brindisi | ............... | A47G 1/1613 248/476 |
| 6,162,201 A * | 12/2000 | Cohen | ............... | A61M 25/0075 604/101.01 |
| 6,196,519 B1 * | 3/2001 | Utterberg | ............ | A61M 39/284 251/10 |
| 6,234,448 B1 * | 5/2001 | Porat | .................... | A61M 39/284 251/10 |
| 6,279,256 B1 * | 8/2001 | Norolof | ................ | A47F 5/0869 211/57.1 |
| 6,349,727 B1 * | 2/2002 | Stewart, Jr. | .......... | A61B 17/122 128/885 |
| D465,843 S | 11/2002 | Guala | | |
| 6,572,588 B1 * | 6/2003 | Bierman | ................ | A61M 25/02 128/DIG. 26 |
| 6,942,647 B2 * | 9/2005 | Nickels | ............... | A61M 39/284 604/250 |
| 7,300,172 B1 * | 11/2007 | Lefler | .................... | A47L 9/2836 362/191 |
| 7,350,761 B1 | 4/2008 | Stuart | | |
| 7,879,013 B2 * | 2/2011 | Smith | ................... | A61M 25/02 604/174 |
| 8,262,639 B2 | 9/2012 | Mathias | | |
| 8,267,370 B2 | 9/2012 | Fisher et al. | | |
| 8,328,763 B2 * | 12/2012 | Traversaz | ......... | A61M 5/14244 604/167.01 |
| 8,636,260 B2 * | 1/2014 | Gauger | ................. | A46B 17/08 248/110 |
| 9,017,296 B2 * | 4/2015 | Beck | ..................... | A61M 39/28 604/246 |
| 9,518,667 B2 * | 12/2016 | Ramos | .................... | F16K 7/063 |
| 10,082,241 B2 * | 9/2018 | Janway | ............... | F16M 13/022 |
| 10,280,955 B2 * | 5/2019 | Mohika | .................. | A61B 50/20 |
| 2002/0161333 A1 * | 10/2002 | Luther | ................ | A61M 39/284 604/167.01 |
| 2003/0074009 A1 * | 4/2003 | Ramsey | ............... | A61B 17/122 606/120 |
| 2004/0092887 A1 | 5/2004 | Nickels | | |
| 2005/0125013 A1 * | 6/2005 | Kessler | .................. | A61B 17/30 606/148 |
| 2005/0215975 A1 * | 9/2005 | Mathias | ................ | A61M 39/08 604/403 |
| 2006/0081797 A1 | 4/2006 | Zerfas | | |
| 2010/0096570 A1 * | 4/2010 | Kashmirian | ........ | A61M 39/284 251/9 |
| 2010/0152681 A1 | 6/2010 | Mathias | | |
| 2010/0232497 A1 | 9/2010 | MacInnis et al. | | |
| 2010/0252702 A1 | 10/2010 | Spang, Jr. et al. | | |
| 2012/0004624 A1 * | 1/2012 | Brown | ................... | A61M 39/287 604/250 |
| 2012/0035553 A1 * | 2/2012 | Lombardo | .......... | A61M 39/284 604/250 |
| 2012/0083803 A1 * | 4/2012 | Patel | ................... | A61B 17/1285 606/142 |
| 2012/0232497 A1 | 9/2012 | Singh | | |
| 2012/0316539 A1 * | 12/2012 | Villasana | ............ | A61M 39/284 604/544 |
| 2013/0066280 A1 | 3/2013 | Wallin | | |
| 2013/0131608 A1 | 5/2013 | Davis et al. | | |
| 2013/0272773 A1 * | 10/2013 | Kamen | ............... | A61M 5/1414 403/11 |
| 2013/0310768 A1 | 11/2013 | Ebara et al. | | |
| 2013/0324975 A1 * | 12/2013 | Douglas | ................ | A61M 39/22 604/544 |
| 2014/0060655 A1 | 3/2014 | Ramos et al. | | |
| 2014/0227021 A1 * | 8/2014 | Kamen | ............... | A61M 5/1414 403/14 |
| 2014/0259548 A1 | 9/2014 | Perullo | | |
| 2016/0355205 A1 * | 12/2016 | Upton | ................... | B62B 3/1424 |
| 2017/0007257 A1 * | 1/2017 | Potter | .................. | A61B 17/122 |
| 2017/0082207 A1 | 3/2017 | Tran | | |
| 2017/0246444 A1 * | 8/2017 | Domatch | .............. | A61M 39/28 |
| 2018/0245699 A1 * | 8/2018 | Lee | ............. | F16K 7/06 |
| 2020/0246012 A1 * | 8/2020 | Shelton, IV | ......... | A61B 17/122 |

FOREIGN PATENT DOCUMENTS

| | | |
|---|---|---|
| EP | 2332611 | 6/2011 |
| EP | 2589395 | 5/2013 |
| FR | 2590645 | 5/1987 |
| JP | S52-052394 | 4/1977 |
| JP | S55-097593 | 7/1980 |
| JP | H02 4384 | 1/1990 |
| JP | H04-193179 | 7/1992 |
| JP | H05329210 | 12/1993 |
| JP | 2000088120 | 3/2000 |
| JP | 2001259030 | 9/2001 |
| JP | 2003245349 | 9/2003 |
| JP | 2006141988 | 6/2006 |
| JP | 2009532137 | 9/2009 |
| JP | 2013176543 | 9/2013 |
| WO | 99/18377 | 4/1999 |
| WO | 2007/112500 | 10/2007 |
| WO | 2007/133291 | 11/2007 |
| WO | 2008/024440 | 2/2008 |
| WO | 2010/109279 | 9/2010 |
| WO | 2011/035367 | 3/2011 |
| WO | 2017/074681 | 5/2017 |

* cited by examiner

PINCH CLAMP DEVICE

RELATED APPLICATIONS

This application claims the benefit of U.S. Provisional Patent Application No. 62/247,615 which was filed on Oct. 28, 2015 and the benefit of U.S. Provisional Patent Application No. 62/296,372 which was filed on Feb. 17, 2016.

BACKGROUND OF THE INVENTION

The pinch clamp is a well-known type of one-piece plastic clamp which is used to close off plastic tubing, such as intravenous tubing. The pinch clamp generally comprises a smooth, hard plastic material that is resilient and capable of controlled flexion to enable engagement and disengagement of the clamping surfaces.

The molding or extrusion process of manufacturing a pinch clamp generally results in the clamp having sharp edges which may scratch or otherwise irritate the patient with which the clamp is used. Further, the hard, smooth properties of the clamp's plastic create difficulty in grasping and manipulating the clamp during use, especially when the clamp becomes wet.

In some instances, the hard, smooth properties of the clamp's plastic further results in unintentional disengagement of the clamp when shear force is applied to the interlocked arms of the clamp. For example and with reference to FIG. 1, a PRIOR ART pinch clamp 1 is shown in a closed or clamped configuration under a shear force. PRIOR ART pinch clamp 1 generally comprises a first arm 2 having a lip 3 configured to selectively engage a terminal end 5 of second arm 4. Clamp 1 is engaged in a clamping configuration when terminal end 5 is received by lip 3. When a shear force 6 is applied to either first or second arms 2 or 4, lip 3 and terminal end 5 may prematurely disengage and release clamping pressure.

Thus, although methods and devices currently exist for clamping a section of tubing using a pinch clamp, challenges still remain. Accordingly, the features of the present invention address and overcome these challenges.

BRIEF SUMMARY OF THE INVENTION

The present invention relates to pinch-style clamps that are designed for use in clamping or occluding plastic tubing, such as intravenous tubing. The pinch clamp of the present invention addresses and overcomes various difficulties known to exist in prior art pinch clamps. For example, some embodiments of the present invention comprise a soft material applied to various surfaces of the pinch clamp to 1) prevent abrasion or irritation to the patient, 2) increase friction between the pinch clamp and the user operating said pinch clamp, 3) increase friction between engaged surfaces of the pinch clamp to prevent premature or unintended disengagement of the clamp, and 4) increase friction between the outer surfaces of the tubing and the clamping surfaces of the clamp.

Some embodiments of the present invention further comprise a dynamic clamping surface or interface that results in positive displacement of fluid in the tubing during the process of engaging the pinch clamp. In particular, some embodiments of the present invention comprise a first clamping surface that is planar and elongated, wherein the first clamping surface is configured to contact and support a first side of the tubing. The pinch clamp further comprises a second clamping surface that is angled and elongated, whereby the second clamping surface comprises a first being spaced from the first clamping surface at a first distance, and further comprises a second end spaced from the first clamping surface at a second distance, wherein the second distance is greater than the first distance.

Upon closing the pinch clamp, the first end of the second clamping surface contact a second side of the tubing to occlude a portion of the tubing interposed between the first clamping surface and the first end of the second clamping surface. Upon further closing motion, the angled surface of the second clamping surface progressively occludes or clamps the tubing along the length of the first clamping surface, thereby positively displacing fluid within the tubing from the interface between the first and second clamping surfaces. Upon full engagement of the pinch clamp, the second end of the second clamping surface is also in contact with the second side of the tubing such that the tubing is occluded or clamped along the entire length of the first and second clamping surfaces.

In a first implementation of the invention, a pinch clamp device is provided comprising a first arm having a first end comprising a lip and a second end comprising a first clamping surface; a second arm having a first end comprising a terminal end and a second end comprising a second clamping surface positioned opposite the first clamping surface; a hinge interconnecting the second end of the first arm and the second end of the second arm; and a material applied to at least one surface of the pinch clamp, the material having a Shore A durometer hardness of from approximately 15 to approximately 100. In some instances, the at least one surface of the pinch clamp is an edge surface.

In some instances, the at least one surface of the pinch clamp is a right-angle surface. In some instances, the at least one surface of the pinch clamp is selected from the group consisting of the lip and the terminal end. Further, in some instances the at least one surface of the pinch clamp is selected from the group consisting of the first clamping surface and the second clamping surface.

In some instances, the pinch clamp device further comprises a plurality of ridges provided on a contact surface of the second arm in proximity to the terminal end. In some instances, the at least one surface of the pinch clamp comprises the plurality of ridges. In some instances, the at least one surface of the pinch clamp comprises an interface surface between the terminal end and the lip. In some instances, the at least one surface of the pinch clamp comprises a contact surface of the pinch clamp. In some instances, the at least one surface of the pinch clamp comprises an interface surface between the first and second clamping surfaces. In some instances, the lip of the pinch clamp comprises a plurality of parallel ridges, each ridge being capable of retaining the terminal end.

In a second implementation of the invention, a pinch clamp device is provided, comprising a first arm having a first clamping surface comprising a planar, elongated surface for supporting a first side of a section of tubing; a second arm having a second clamping surface positioned opposite the first clamping surface and comprising an angled, elongated surface, the second clamping surface having a first end and a second end, the first end being spaced from the first clamping surface at a first distance and the second end being spaced from the first clamping surface at a second distance, the second distance being greater than the first distance; and a hinge interconnecting the first and second arms.

In some instances, first end of the second clamping surface is configured to contact a second side of the tubing prior to the second end of the second clamping surface contacting the second side of the tubing during a process of closing the pinch clamp to clamp the tubing. In some instances, the second end of the second clamping surface is configured to contact the second side of the tubing when the first and second arms of the pinch clamp are fully engaged. In some instances, the device further comprises a material applied to at least one surface of the pinch clamp, the material having a Shore A durometer hardness of from approximately 15 to approximately 100. In some instances, the at least one surface is an interface between the pinch clamp and the tubing. In some instances, the at least one surface is selected from the group consisting of the first clamping surface and the second clamping surface. In some instances, the at least one surface is a contact surface of the pinch clamp.

In a third implementation of the invention, a pinch clamp device is provided, comprising a first arm having a first end comprising a lip and a second end comprising a first clamping surface, the first clamping surface comprising a planar, elongated surface for supporting a first side of a section of tubing; a second arm having a first end comprising a terminal end and a second end comprising a second clamping surface positioned opposite the first clamping surface, the second clamping surface comprising an angled, elongated surface; a hinge interconnecting the second end of the first arm and the second end of the second arm; and a material applied to at least one surface of the pinch clamp, the material having a Shore A durometer hardness of from approximately 15 to approximately 100. In some instances, the second clamping surface comprises a first end and a second end, the first end being spaced from the first clamping surface at a first distance and the second end being spaced from the first clamping surface at a second distance, wherein the second distance is greater than the first distance.

In a fourth implementation of the invention, a pinch clamp device is provided, comprising a first arm having a first end comprising a lip and a second end comprising a first clamping surface; a second arm having a first end comprising a terminal end and a second end comprising a second clamping surface positioned opposite the first clamping surface; and a hinge interconnecting the second end of the first arm and the second end of the second arm. In some instances, the pinch clamp device further comprises a nesting component comprising opposing sidewalls coupled together via an interconnect, the interconnect being sized to fit inside of the hinge and to position the opposing sidewalls outside and adjacent to the first and second arms. In some instances, the nesting component further includes a raised feature on an interior surface of one or more of the opposing sidewalls, the raised feature contacting one or both of the first and second arms to limit rotation of the nesting component. In some instances, one of the first or second clamping surfaces is formed as a recessed surface between raised surfaces. In some instances, the pinch clamp device further comprises extensions that extend from opposing sides of one of the first or second arms. In some instances, the extensions are coupled together via a rounded interconnect, the rounded interconnect forming an opening through which tubing passes between the extensions. In some instances, the first end of the second arm includes a second hinge. In some instances, the second hinge allows the terminal end of the second arm to pivot towards the hinge that interconnects the first and second arm. In some instances, the first or second arms includes extensions positioned on opposing sides of the arm and the other of the first or second arms includes an inner extension that inserts between the opposing extensions when the pinch clap device is engaged. In some instances, the first arm includes raised surfaces positioned on each side of the first clamping surface, the second clamping surface inserting between the raised surfaces when the pinch clamp device is engages.

In some instances, the hinge forms an elliptical-shaped opening between the hinge and the first and second clamping surfaces. In some instances, the outer edges of the first and second arms are rounded. In some instances, the terminal end of the second arm forms an interface surface having ends that protrude outwardly beyond the rounded outer edges of the second arm. In some instances, one of the first or second clamping surfaces includes lateral posts and the other of the first or second clamping surfaces includes recessed surfaces that are positioned between the lateral posts when the first and second clamping surfaces are engaged.

In some instances, the terminal end of the second arm forms an interface surface that includes outwardly facing recessed surfaces and the first arm includes inwardly facing lateral protrusions between which the recessed surfaces are positioned when the interface surface is secured under a ledge formed by the lip. In some instances, the first arm includes a recessed section positioned below the first clamping surface, the device further comprising a lateral disengagement prevention component having a bottom section and two opposing arms that extend upwardly from opposite ends of the bottom section; wherein the recessed section is configured to accommodate the lateral disengagement prevention component such that the opposing arms are positioned overtop the second arm. In some instances, each opposing arm includes an inward protrusion that extends from an inner surface of the arm, each inward protrusion being positioned such that a bottom surface of the inward protrusion contacts a top surface of the first arm when the bottom surface of the lateral disengagement prevention component is position within the recessed section.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

The present invention relates to pinch-style clamps that are designed for use in clamping or occluding plastic tubing, such as intravenous tubing. The pinch clamp of the present invention addresses and overcomes various difficulties known to exist in prior art pinch clamps. For example, some embodiments of the present invention comprise a soft material applied to various surfaces of the pinch clamp to 1) prevent abrasion or irritation to the patient, 2) increase friction between the pinch clamp and the user operating said pinch clamp, 3) increase friction between engaged surfaces of the pinch clamp to prevent premature or unintended disengagement of the clamp, and 4) increase friction between the outer surfaces of the tubing and the clamping surfaces of the clamp.

Some embodiments of the present invention further comprise a dynamic clamping surface or interface that results in positive displacement of fluid in the tubing during the process of engaging the pinch clamp. In particular, some embodiments of the present invention comprise a first clamping surface that is planar and elongated, wherein the first clamping surface is configured to contact and support a first side of the tubing. The pinch clamp further comprises a second clamping surface that is angled and elongated, whereby the second clamping surface comprises a first being spaced from the first clamping surface at a first distance, and further comprises a second end spaced from the first clamping surface at a second distance, wherein the second distance is greater than the first distance.

Upon closing the pinch clamp, the first end of the second clamping surface contact a second side of the tubing to occlude a portion of the tubing interposed between the first clamping surface and the first end of the second clamping surface. Upon further closing motion, the angled surface of the second clamping surface progressively occludes or clamps the tubing along the length of the first clamping surface, thereby positively displacing fluid within the tubing from the interface between the first and second clamping surfaces. Upon full engagement of the pinch clamp, the second end of the second clamping surface is also in contact with the second side of the tubing such that the tubing is occluded or clamped along the entire length of the first and second clamping surfaces.

Figure 2A:
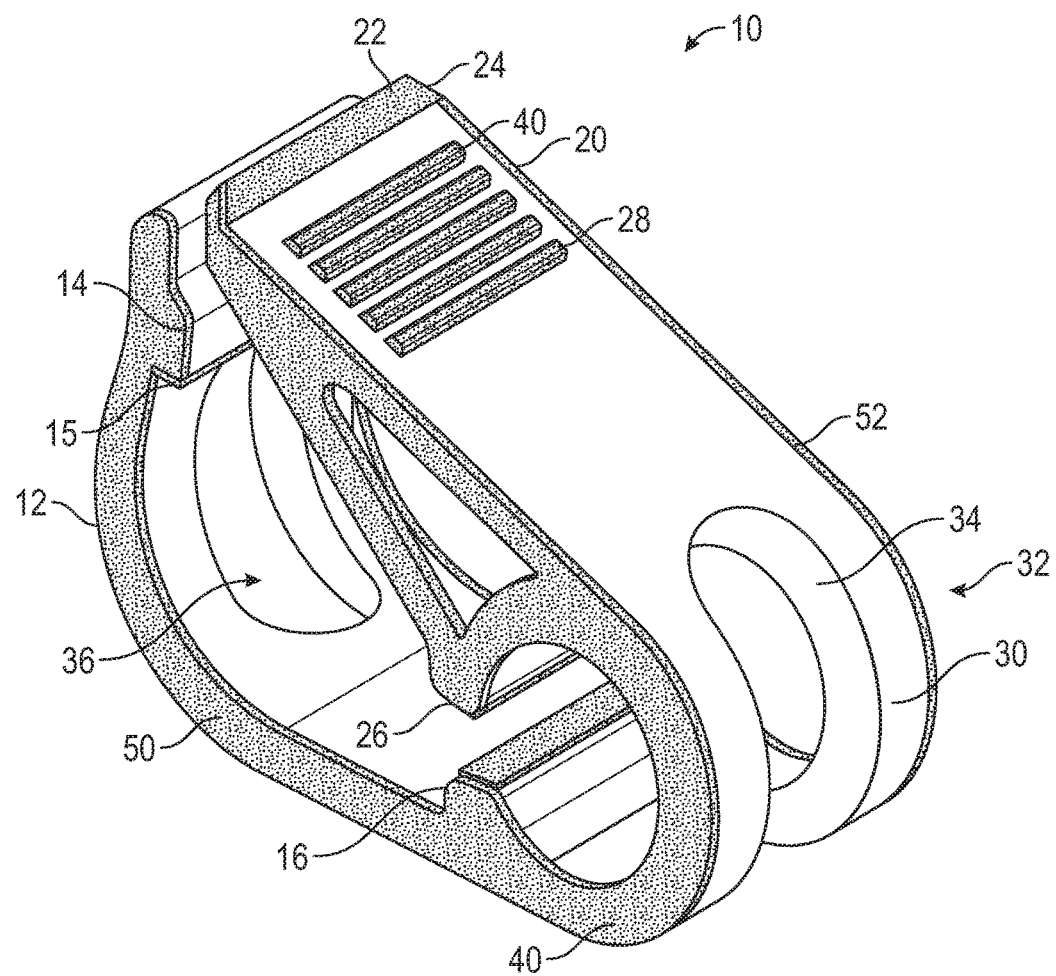
FIG. 2A illustrates a perspective view of a pinch clamp in a disengaged configuration in accordance with a representative embodiment of the present invention.

FIG. 2A illustrates a perspective top and side view of a pinch clamp 10. Pinch clamp 10 generally comprises a first arm 12 having a first end comprising a lip 14 forming a ledge 15. In some instances, lip 14 comprises a plurality of parallel ledges or ridges. First arm 12 further comprises a second end comprising a first clamping surface 16. In some instances, first clamping surface 16 comprises a raised surface having a width that is approximately equal to a width of clamp 10. In some instances first clamping surface 16 is planar or generally flat. In other instances, first clamping surface 16 is angled, rounded, pointed, ridged, grooved, or any combination thereof.

Pinch clamp 10 further comprises a second arm 20 having a first end comprising a terminal end 24. Terminal end 24 is generally configured to engage with lip 14 to secure clamp 10 in an engaged configuration. In some instances terminal end 24 comprises a blunt, square end. In some embodiments, terminal end 24 comprises a wedged or tapered shape, such that terminal end 24 tapers outwardly to a tip or pointed edge. Terminal end 24 further comprises an interface surface 22 that is configured to compatibly engage with ledge 15 of lip 14 so as to hold clamp 10 in an engaged configuration.

In some embodiments, second arm 20 comprises a second end having a second clamping surface 26. Second clamping surface 26 is generally positioned opposite of first clamping surface 16, as is common for pinch clamps. In some instances, second clamping surface 26 is tapered such that in a disengaged configuration a first end of clamping surface 26 is spaced from clamping surface 16 at a first distance, and a second end of clamping surface 26 is spaced from clamping surface 16 at a second distance, the second distance being greater than the first distance. In one embodiment, the second end of clamping surface 26 is closest to the first end 24 of second arm 20, and the first end of clamping surface 26 is in proximity to a closed end 32 of clamp 10.

The second ends of first and second arms 12 and 20 are interconnected via a hinge 30. In some instances, hinge 30 comprises a rounded extension of the second ends of first and second arms 12 and 20. Hinge 30 is configured to position first arm 12 opposite second arm 20. In some instances, hinge 30 comprises a relaxed position (as shown in FIG. 2) and a tensioned position (not shown). In the relaxed position, hinge 30 positions first and second arms 12 and 20 to provide a gap or space between first and second clamping surfaces 16 and 26. The relaxed position of hinge 30 further maintains a gap or space between terminal end 24 and lip 14. In some instances, hinge 30 further comprises a window or opening 34 through which tubing is passed. First arm 12 further comprises a window or opening 36 that is generally aligned with window 34 and configured to accommodate tubing.

In some embodiments, a contact or exterior surface 26 of second arm 20 further comprises a grip feature 28. Grip feature 28 is generally provided to increase friction between a user's thumb or finger and pinch clamp 10 during use. In some instances, grip feature 28 comprises a plurality of parallel ridges or raised features. In some embodiments, grip feature 28 comprises a texture or other surface treatment intended to increase friction. In some instances, grip feature 28 further provides a visual and/or tactile reference indicating how and where the user should grip the clamp 10.

Some embodiments of the present invention further comprise a soft, polymer material 40 applied to various surfaces of pinch clamp 10. As used herein, the term "soft, polymer material" is understood to include any material that may be applied or added to a plastic material suitable for use in manufacturing pinch clamp 10, wherein the soft, polymer material comprises a Shore A durometer hardness that is less than the plastic material of which the pinch clamp is constructed. For example, in some embodiments a soft, polymer material comprises a Shore A durometer hardness of from approximately 15 to 100, from approximately 20 to 80, from approximately 30 to 70, from approximately 40 to 60, from approximately 45 to 55, or approximately 50. In some instances, a soft, polymer material comprises a Shore A durometer hardness of less than 15. In some instances, a soft, polymer material comprises a Shore A durometer hardness of greater than 100.

Non-limiting examples of soft, polymer materials include thermoplastic elastomers such as thermoplastic rubbers, copolymers or physical mixes of polymers such as a plastic and a rubber, crosslinked polymers, styrenic block copolymers, polyolefin blends, elastomeric alloys, thermoplastic polyurethanes, thermoplastic copolyester, thermoplastic polyamides, or combinations thereof.

For example, in some instances a soft, polymer material is applied as a thin coating to the rigid or semi-rigid material of the pinch clamp. In some instances, soft, polymer material pieces are first produced by a known process, such as extrusion or injection molding. The polymer pieces are then applied to one or more surfaces of the pinch clamp, such as by an adhesive, mechanical interference, or interlocking features or surfaces. In some instances, one or more surfaces of the rigid or semi-rigid material of the pinch clamp is removed and replaced by the polymer pieces to provide a final profile and shape for the pinch clamp. In some embodiments, the pinch clamp is provided in a two-shot molding process, wherein a first injection unit is provided to mold the rigid or semi-rigid material of the clamp, and a second injection unit is provided to apply the soft, polymer material in strategic locations. In some instances, one or more surfaces of the rigid or semi-rigid material of the pinch clamp is removed and replaced by the polymer material or pieces to soften one or more contact surfaces. In some instances, one or more surfaces of the rigid or semi-rigid material of the pinch clamp is removed and replaced by the polymer material or pieces to increase friction between two or more surfaces of the clamp, or between one or more surfaces of the clamp and a section of tubing inserted within the clamp.

In some instances, a soft, polymer material 40 is applied to various surfaces of pinch clamp 10 to soften various surfaces of pinch clamp 10 that may otherwise scratch or irritate a patient's skin. For example, in one embodiment a soft, polymer material 40 is applied to an edge or side surface 50 of pinch clamp 10. In one embodiment, a soft, polymer material 40 is applied to a right-angled surface 52 of pinch clamp 10. Further, in one embodiment a soft, polymer material 40 is applied to a contact surface, wherein a "contact surface" is understood to include any exposed surface that may contact a patient during use. In some instances, a soft, polymer material 40 is applied to all exterior surfaces of pinch clamp 10.

In some instances, a soft, polymer material 40 is applied to various surfaces to increase friction. For example, in one embodiment a soft, polymer material 40 is applied to a grip feature 28 of pinch clamp 10, whereby to increase friction between the user's thumb or finger and pinch clamp 10. In one embodiment, a soft, polymer material 40 is applied to at least one of the first and second clamping surfaces 16 and 26, whereby to increase friction between the clamping surfaces and tubing secured therebetween.

Figure 1:
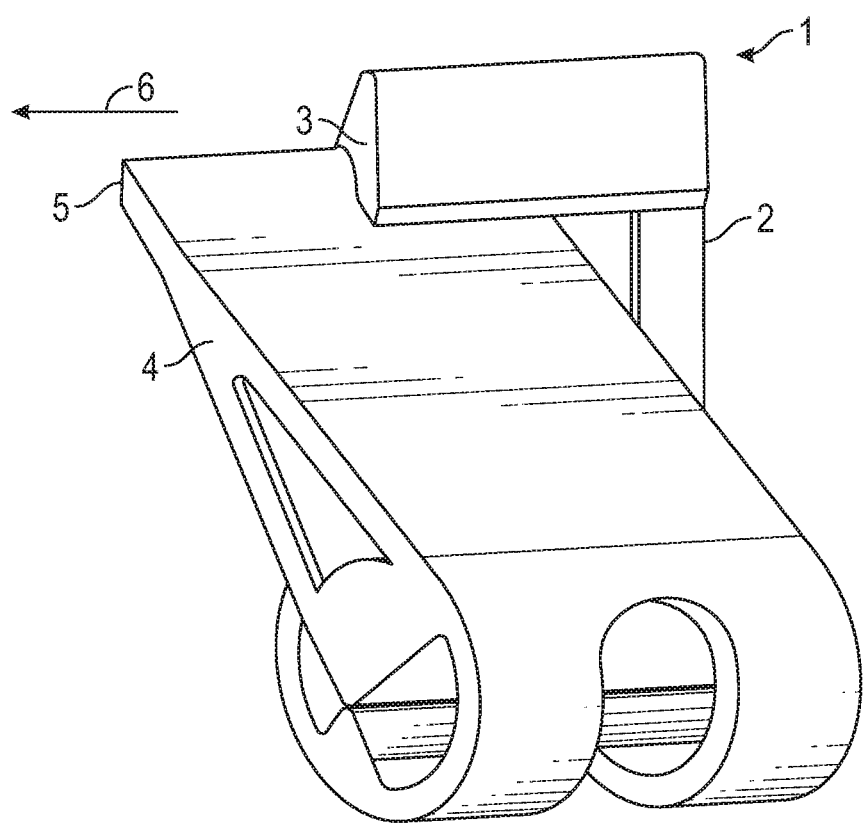
FIG. 1 illustrates a perspective view of a PRIOR ART pinch clamp in a skewed configuration under shear force.
Figure 2B:
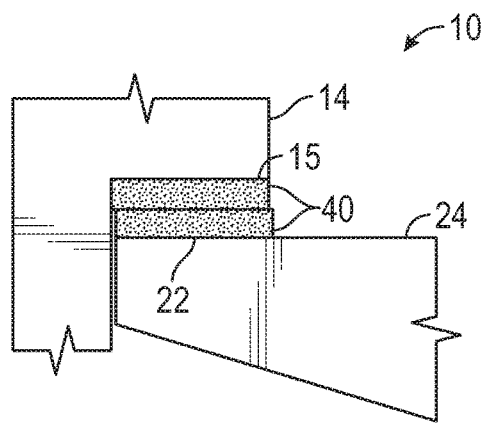
FIG. 2B illustrates a detailed plan side view of a pinch clamp in an engaged configuration in accordance with a representative embodiment of the present invention.

In one embodiment, a soft, polymer material 40 is applied to at least one of lip 14 and terminal end 24 to increase friction therebetween. As previously discussed in connection with the PRIOR ART clamp 1 of FIG. 1, the hard plastic interface between lip 3 and terminal end 5 enables skewing of first and second arms 2 and 4 when a shear force 6 is applied to the clamp 1. This may result in premature or unintended disengagement of clamp 1. In contrast, the soft, polymer material 40 interface between lip 15 and terminal end 24 increases friction between these surfaces, thereby preventing unintended disengagement. A detailed view of these surfaces is shown in FIG. 2B.

Figure 3A:
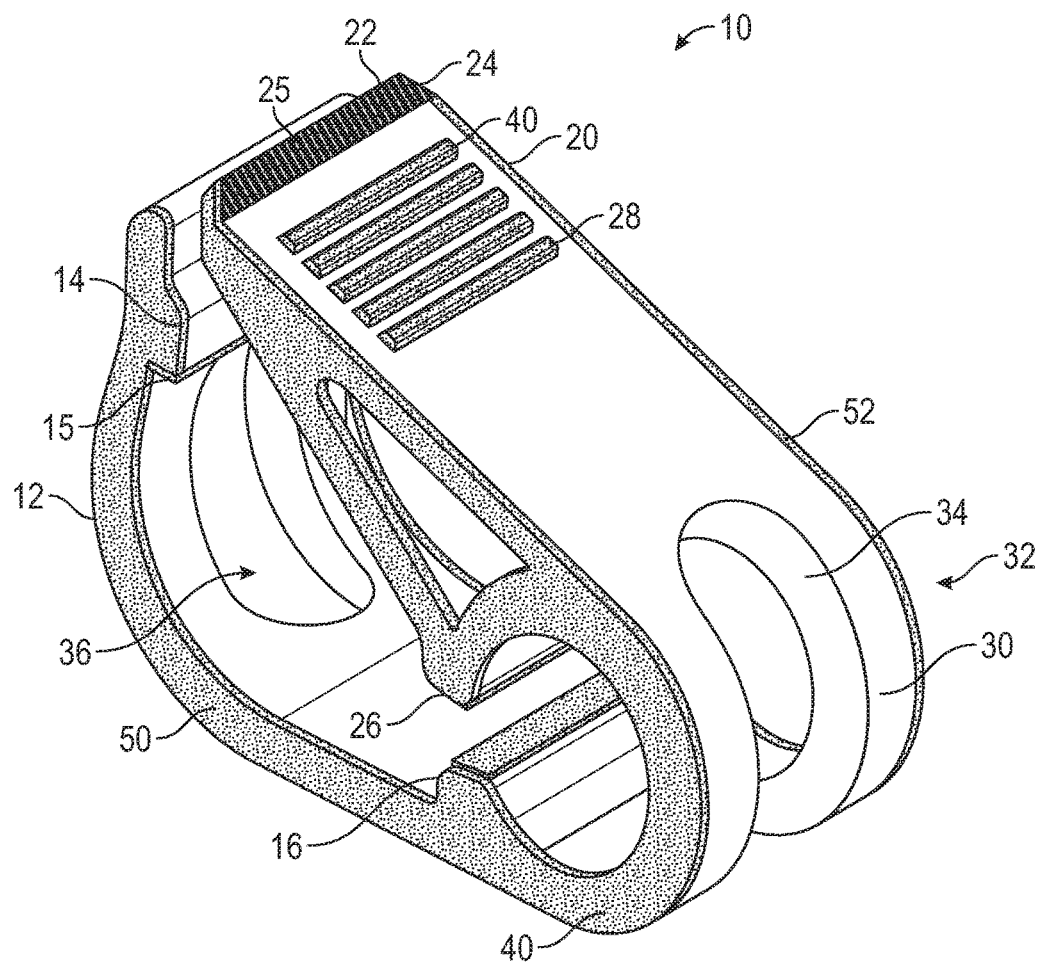
FIG. 3A illustrates a perspective view of a pinch clamp in a disengaged configuration and further comprising a plurality of grooves on the interface surface in accordance with a representative embodiment of the present invention.
Figure 3B:
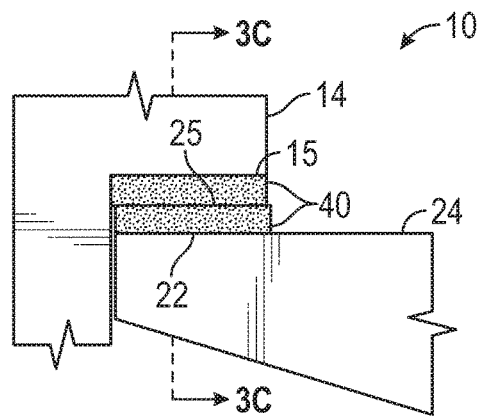
FIG. 3B illustrates a detailed plan side view of a pinch clamp in an engaged configuration and comprising a plurality of grooves on the interface surface in accordance with a representative embodiment of the present invention.
Figure 3C:
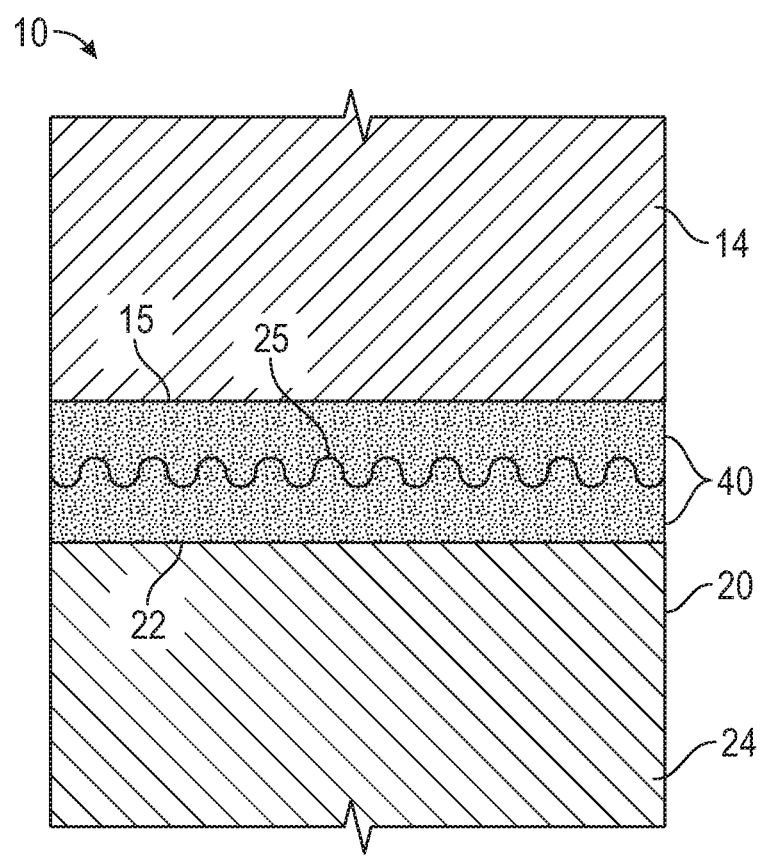
FIG. 3C illustrates a cross-section end view of a pinch clamp in an engaged configuration and comprising a plurality of grooves on the interface surface in accordance with a representative embodiment of the present invention.

In some embodiments, at least one surface of lip 15 and terminal end 24 further comprise a mechanical feature or surface 25 configured to further increase lateral or axial friction at interface surface 22, as shown in FIGS. 3A-3C.

For example, in one embodiment interface surface 22 has a mechanical feature 25 comprising a plurality of interlocking grooves. In some instances, mechanical feature 25 provides alignment between first and second arms 14 and 20. In some instances, mechanical feature 25 comprises micro-features, such as a texture. In some embodiments, mechanical feature 25 comprises a micro-feature that is perpendicular, parallel, or perpendicular and parallel to the direction of tubing threaded through clamp 10. In some instances, mechanical feature 25 is formed in the rigid polymer material of clamp 10, and subsequently coated or covered with a soft, polymer material 40. In other instances, mechanical feature 25 is provided directly in soft, polymer material 40.

Referring now to FIGS. 4A-4D, some embodiments of the present invention comprise a dynamic clamping surface or interface 55 that results in positive displacement of fluid 60 within the tubing 70 being clamped. Positive displacement of fluid 60 may be desirable where fluid 60 comprises a medication that would remain in tubing 70 except for being advanced into the patient via positive displacement.

Figure 4A:
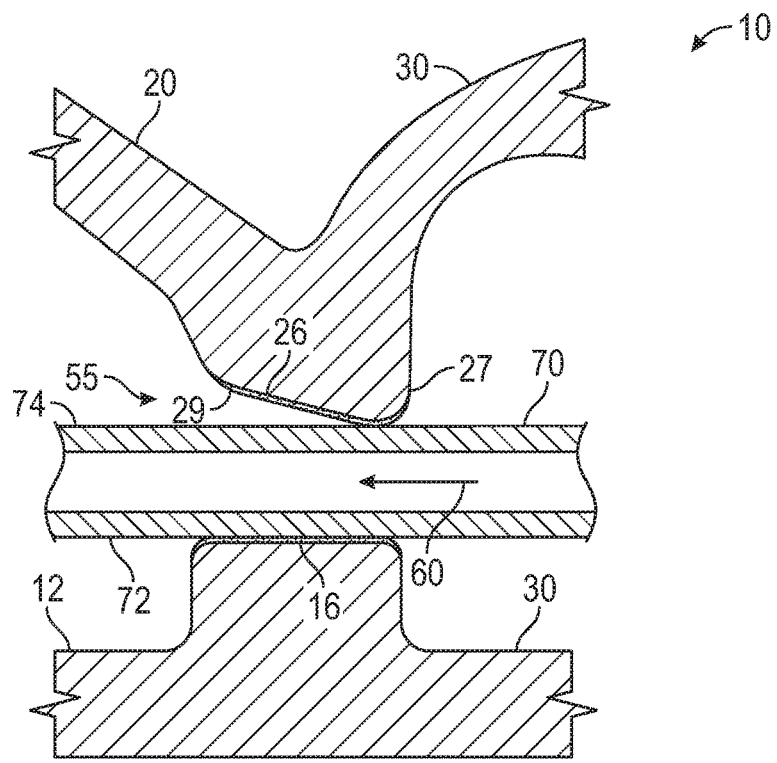
FIG. 4A-4D illustrates detailed plan side views of first and second clamping surfaces during the process of clamping a section of tubing in accordance with a representative embodiment of the present invention.

With reference to FIG. 4A, pinch clamp 10 is shown in a disengaged configuration, whereby a first side 72 of tubing 70 is supported on the entire, elongated first clamping surface 16 of first arm 12. Further, a first end 27 of second clamping surface 26 is positioned in proximity to, or lightly in contact with a second side 74 of tubing 70.

In some embodiments, first clamping surface 16 is generally planar and elongated such that surface 16 supports a length of tubing 70. In contrast, second clamping surface 26 is angled such that a first end 27 is positioned lower than, or closer to first clamping surface 16 that is the position of second end 29. As such, second clamping surface tapers outwardly or upwardly from first end 27 to second end 29, or from the proximal end to the distal end of second clamping surface 26.

Tubing 70 is not compressed or occluded when pinch clamp 10 is in a disengaged configuration. Rather, tubing 70 is freely moveable between first and second clamping surfaces 16 and 26. In some embodiments, first and second clamping surfaces 16 and 26 further comprise a soft, polymer material (not shown) that increases friction between tubing 70 and the clamping surfaces such that pinch clamp 10 is prevented from freely sliding along the length of tubing 70. Rather, pinch clamp 10 must be manually adjusted by a user to a desired position on tubing 70, after which clamp 10 maintains its position by friction between the soft, polymer material and the outer surface of tubing 70.

In some embodiments, the soft, polymer material (not shown) further provides a cushioning function between the rigid plastic material of pinch clamp 10 and the pliable plastic material of tubing 70. In some instances, this cushioning function enables full occlusion of tubing 70 while preventing hard kinking that may weaken the tubing structure. In some instances, this cushioning function improves tubing recovery upon release of pinch clamp 10.

Figure 4B:
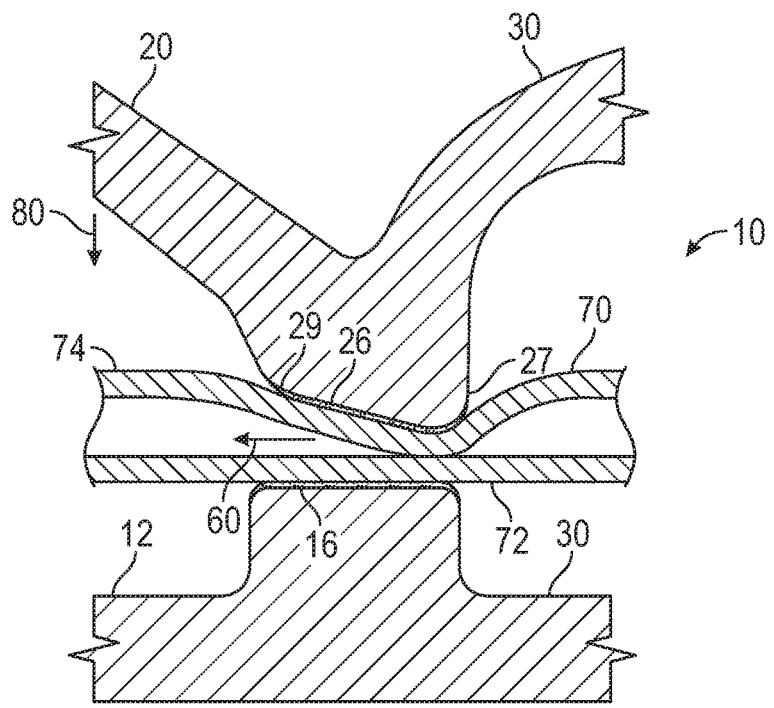

Referring now to FIG. 4B, pinch clamp 10 is moved from a disengaged configuration to a partially engaged configuration as second arm 20 is moved in a downward direction 80 and tubing 70 is pinched between first end 27 of second clamping surface 26 and a proximal end of first clamping surface 16. Thus, a portion of tubing 70 located between first and second clamping surfaces 16 and 26 is occluded, and a portion of this section of tubing 70 is also unoccluded.

Figure 4C:
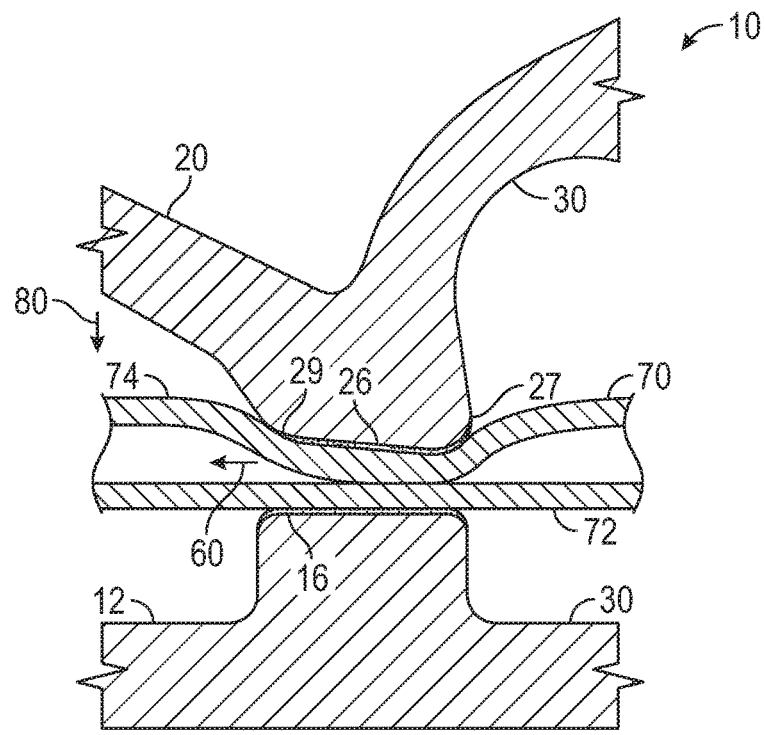

As first arm 20 is further advanced in downward direction 80, the distance between the remaining surfaces of second clamping surface 26 and first clamping surface 16 is gradually reduced as the second end 29 descends towards first clamping surface 16, as shown in FIG. 4C. This gradual occlusion forces or positively displaces fluid 60 out from between the clamped surfaces thereby advancing fluid 60 through the distal section of tubing 70. In some instances, the displaced fluid 60 is infused into a patient via an intravenous catheter coupled to tubing 70.

Figure 4D:
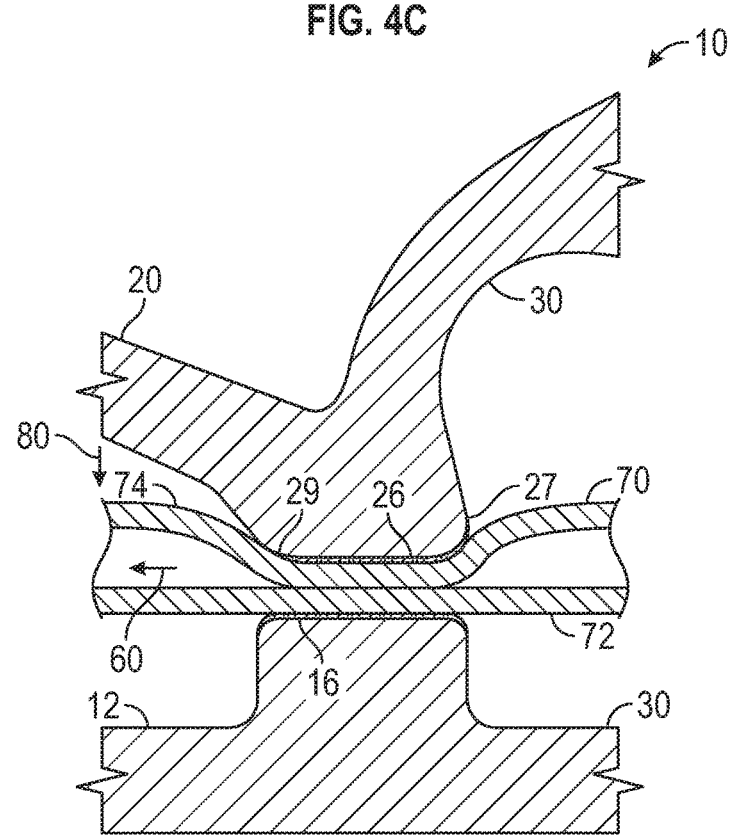

First arm 20 is further advanced in downward direction 80 until distal end 24 is received by lip 14, thereby fully engaging pinch clamp 10, as discussed previously. Upon full engagement, tubing 70 is fully clamped between second end 29 of second clamping surface 26 and first clamping surface 16, as shown in FIG. 4D. In some instances, first end 27 and second end 29 are approximately equally distanced from first clamping surface 16 when pinch clamp 10 is fully engaged. Following full engagement of pinch clamp 10, the positive displacement of fluid 60 is complete.

In some embodiments, second arm 20 flexes or pivots about the contact point between first end 27 and first clamping surface 16, such that clamping pressure or contact between second clamping surface 26 and tubing 70 is applied in a linear fashion. In come embodiments, hinge 30 is configured to bend and adjust laterally to facilitate linear application of compression force between first and second clamping surfaces 16 and 26.

Figure 5:
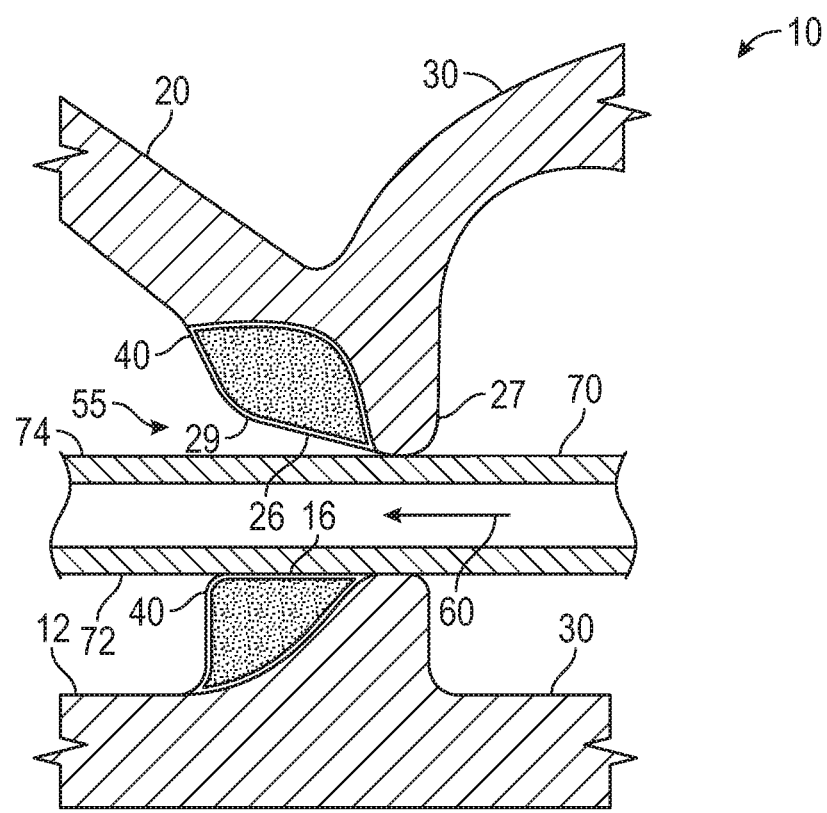
FIG. 5 illustrates a detailed plan side view of first and second clamping surfaces, wherein the clamping surfaces comprise a rigid or semi-rigid material and a soft, polymer material in accordance with a representative embodiment of the present invention.

In some embodiments, at least one of first and second clamping surfaces 16 and 26 further comprise a proximal end comprising or consisting of a rigid or semi-rigid material, and further comprising a distal end comprising or consisting of a soft, polymer material 40, as shown in FIG. 5. This embodiment has the benefit of providing a robust primary or proximal clamping interface, while having a softer distal clamping interface to compress the internal volume of the tubing, while preventing over-compression of the tubing over the full length of the clamping surface. In some instances, the rigid or semi-rigid proximal end material further reduces friction between pinch clamp and tubing 70 when in the disengaged configuration, thereby permitting easy movement of clamp 10 along the length of tubing 70.

Figure 6A:
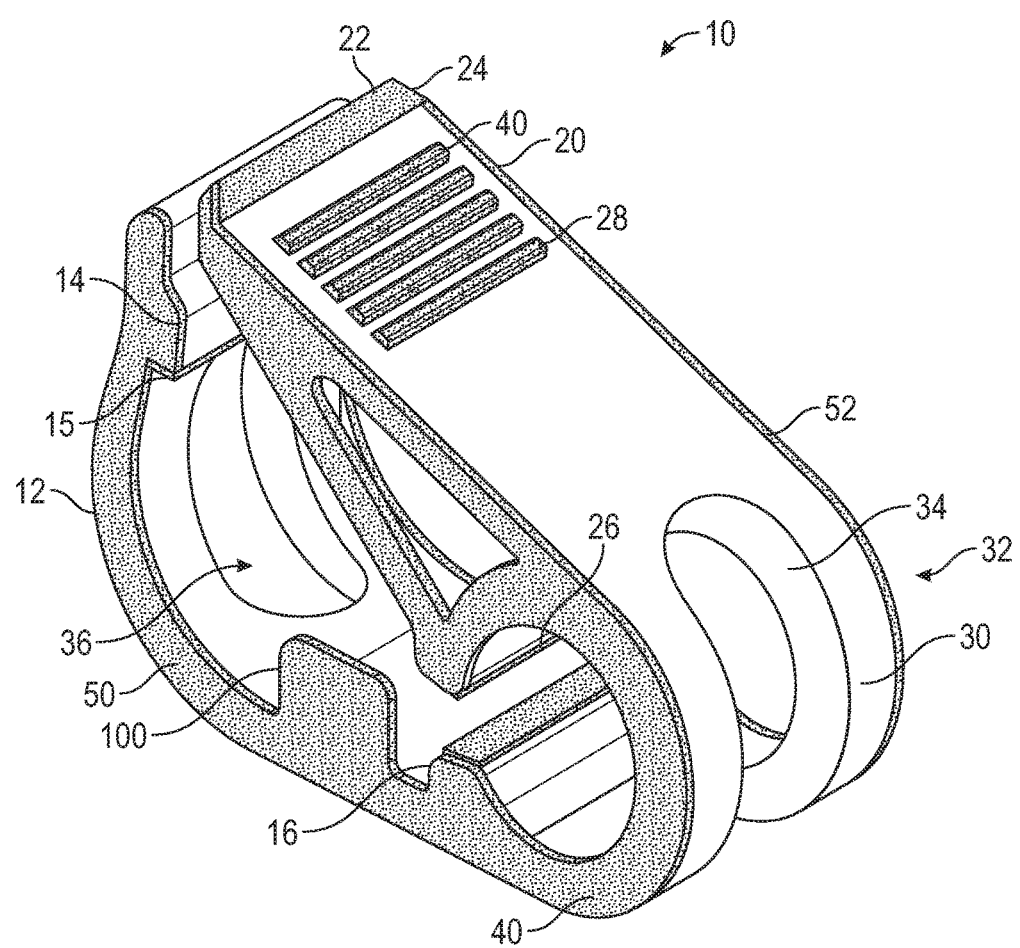
FIGS. 6A-6C illustrate perspective views of a pinch clamp in a disengaged configuration and further having one or more extensions to retain a tube within the pinch clamp in accordance with various representative embodiments of the present invention.
Figure 6B:
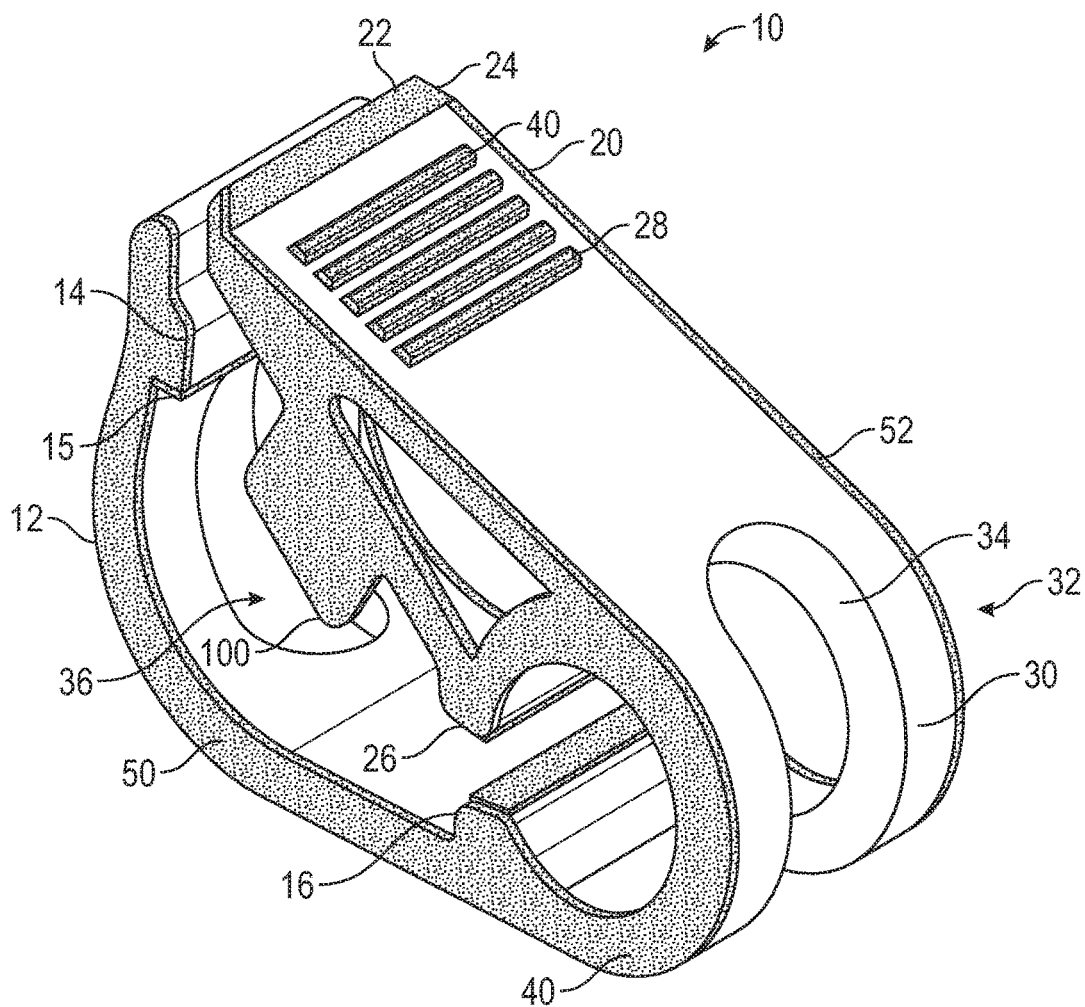
Figure 6C:
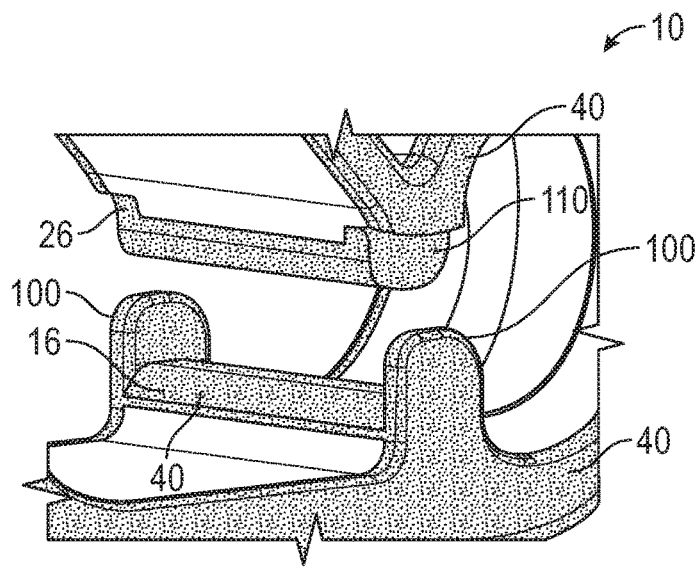

In some instances, and prior to clamping, tube 70 may exit pinch clamp 10 laterally between first and second arms 12 and 20. Accordingly, some embodiments of the present invention further provide one or more extensions 100 to retain a tube within pinch clamp 10, as shown in FIGS. 6A-6C. In some instances, a portion of the outer edge surface of first arm 12 is extended upwardly towards second arm 20 to provide a wall or extension 100, as shown in FIG. 6A. In some instances, a portion of the outer edge surface of second arm 20 is extended downwardly towards first arm 12 to provide a wall or extension 100, as shown in FIG. 6B. In some embodiments, pinch clamp 10 comprises two or more extensions 100. In one embodiment, pinch clamp 10 comprises a first extension 100 on a first side of second arm 20, and a second extension 100 on a second side of second arm 20, wherein the second side is opposite the first side. In one embodiment, pinch clamp 10 comprises a first and second extension 100 on opposite sides of first arm 12. Further, in some embodiments, pinch clamp 10 comprises first and second extensions on opposite sides of first arm 12, and further comprises first and second extensions 100 on opposite sides of second arm 20, wherein the extensions overlap, abut, or close a distance between one another when clamp 10 is in an engaged configuration.

Extension 100 is configured to at least partially close the gap between first and second arms 12 and 20 when in the engaged or disengaged configurations. In some instances, extension 100 is a thin fin or plate or rigid or semi-rigid material. In some instances, extension 100 is a thin fin or plate of soft, polymer material 40. In some instances, extension 100 is a thin fin or plate of rigid or semi-rigid material onto which is applied a soft, polymer material 40. Referring now to FIG. 6C, in some embodiments the outward edges of first clamping surface 16 further comprises one or more extensions 100 that extend upwardly towards second clamping surface 26. Further, the outer edges of second clamping surface 26 comprise one or more recesses or notches 110 configured to receive the one or more extensions 100 when pinch clamp 10 is engaged. The interaction between extensions 100 and recesses 110 retains tube 70 within the clamping surfaces when clamp 10 is engaged. In some instances, portions of the rigid or semi-rigid material of clamp 10 is removed and replaced by soft, polymer material 40 to provide one or more of first and second clamping surfaces 16 and 26, extensions 100, and recesses 110.

FIGS. 7A-12 illustrate a number of different variations of a pinch clamp in accordance with one or more embodiments of the present invention. Each of these pinch clamps includes the same general structure as pinch clamp 10. Therefore, many of the components of each pinch clamp will not be redundantly described. However, similar references will be employed to refer to these similar structures. Also, although the figures depict various specific embodiments that include one or more variations, these variations could be employed in addition to or in placed of features of any of the other described embodiments of pinch clamps.

FIGS. 7A-7D illustrate an embodiment of a pinch clamp 700 that is similar to pinch clamp 10 but employs a nesting component 701 to prevent the lateral disengagement of second arm 20 from first arm 12. In other words, nesting component 701 can prevent relative movement between first arm 12 and second arm 20 in a direction that is substantially perpendicular to the longitudinal axis of the tubing to which pinch clamp 700 may be coupled. As a result, by including nesting component 701, pinch clamp 700 (or other similar embodiments of pinch clamps that include a nesting component) will likely only become disengaged when the clinician intentionally applies a downward/outward force on the terminal end of first arm 12.

Figure 7A:
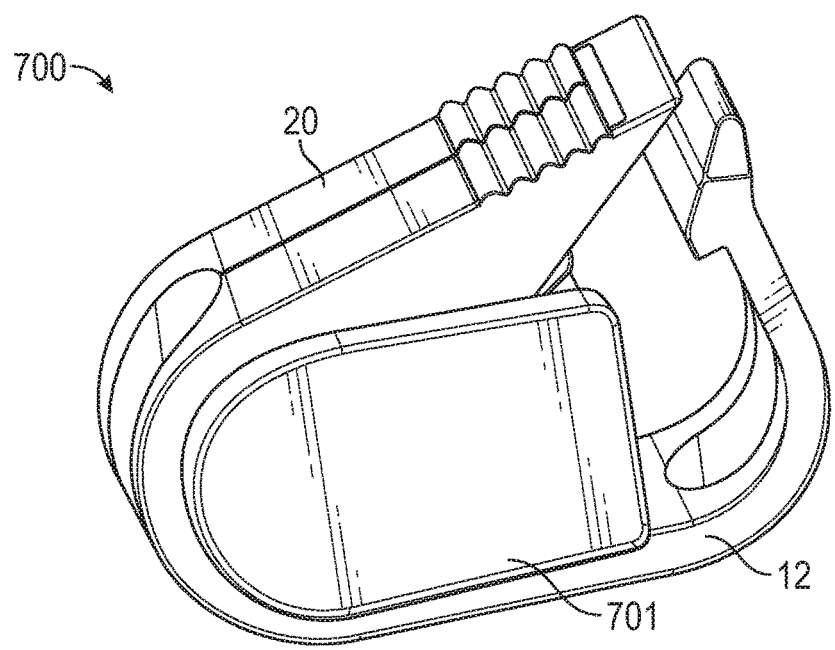
FIGS. 7A-7D illustrate perspective and cross-section views a pinch clamp having a nesting component for preventing lateral disengagement in accordance with a representative embodiment of the present invention.
Figure 7B:
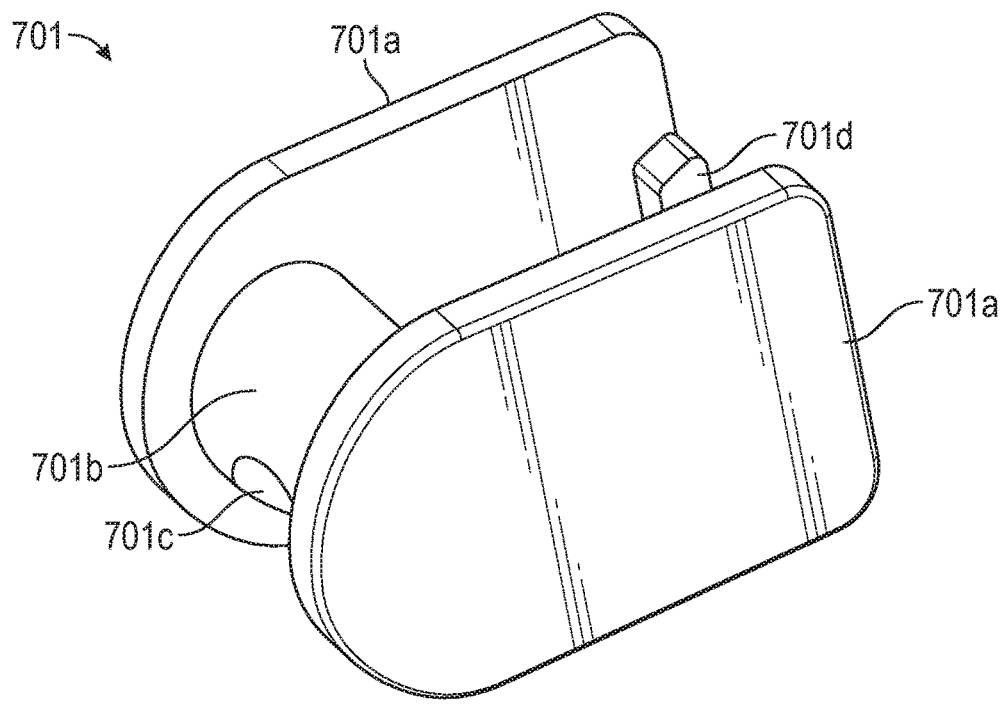

As is better shown in FIG. 7B, which depicts nesting component 701 in isolation, nesting component 701 comprises opposing sidewalls 701a that are coupled together via interconnect 701b. The width/diameter of interconnect 701b can be configured to allow the interconnect to sit within opening 712 formed between the hinge and clamping surfaces, while the length of interconnect 701b can be configured such that sidewalls 701a are positioned immediately outside the outer surfaces of first arm 12 and second arm 20. The size of sidewalls 701a (i.e., the amount by which sidewalls 701a extend away from interconnect 701b in any direction) can be sufficient to cause the sidewalls to overlap first arm 12 and second arm 20 thereby confining lateral movement of the two arms.

Interconnect 701b can include an opening 701c that generally aligns with opening 34 to accommodate tubing that may extend through pinch clamp 700. Also, one or both of the inner surfaces of sidewalls 701a can include a raised feature 701d that functions to limit rotation of nesting component 701 with respect to pinch clamp 700. In some embodiments, sidewall 701a can have a size sufficient to cause raised feature 701d to be positioned on an opposite side of the clamping surfaces from interconnect 701b. For example, FIG. 7D illustrates how raised feature 701d would be positioned to cause the feature to contact an inside surface of first arm 12 or second arm 20 when nesting component 701 is rotated. In this way, raised feature 701d minimizes the likelihood that opening 701c may kink or otherwise occlude the tubing.

Figure 7C:
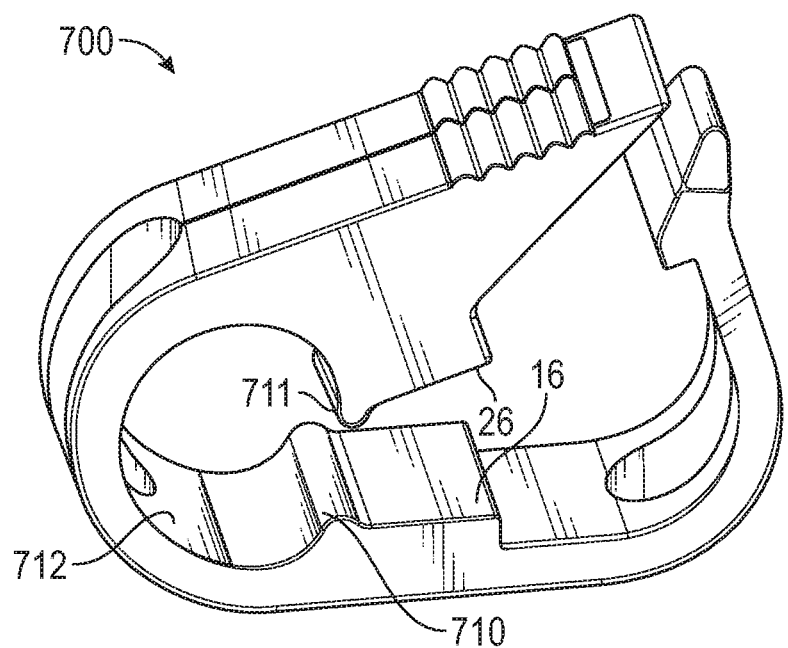
Figure 7D:
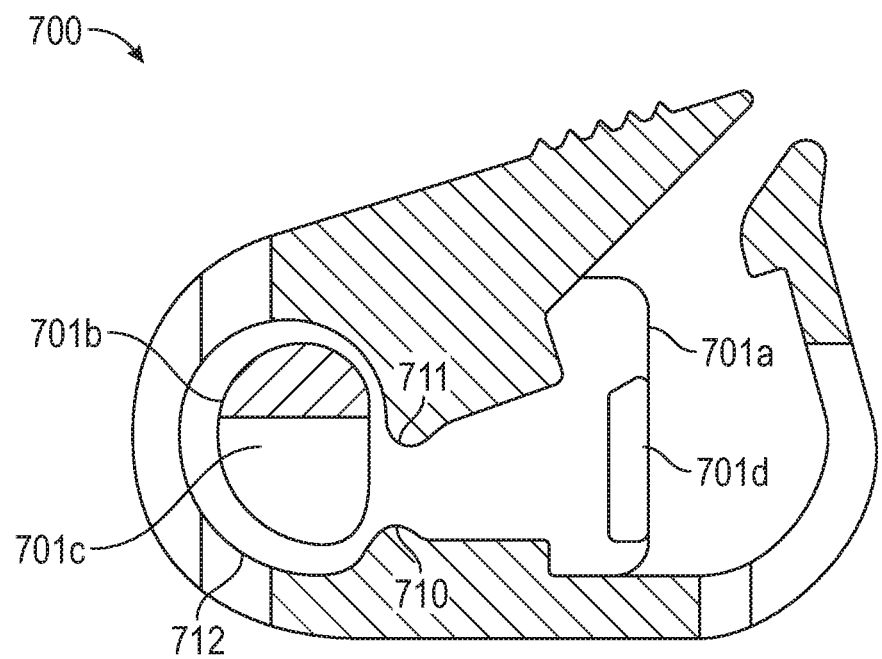

FIG. 7C, which shows pinch clamp 700 without nesting component 701, and FIG. 7D, which illustrates a cross-sectional side view of pinch clamp 700 containing nesting component 701, illustrate how pinch clamp 700 (or other similar pinch clamps) can include clamping surfaces that provide positive displacement. As shown, first clamping surface 16 and second clamping surface 26 include protrusions 710 and 711 respectively. In these figures, protrusions 710 and 711 are shown at the left or proximal end of the clamping surfaces. Protrusions 710 and 711 function in a similar manner as the dynamic clamping surfaces depicted in FIGS. 4A-4D. In particular, as pinch clamp 700 is engaged, protrusions 710 and 711 will contact the tubing prior to the remaining portions of first and second clamping surfaces 16 and 26. Accordingly, as pinch clamp 700 becomes fully engaged, fluid within the tubing will be forced in a distal direction (or in a rightward direction in FIG. 7D).

Figure 8A:
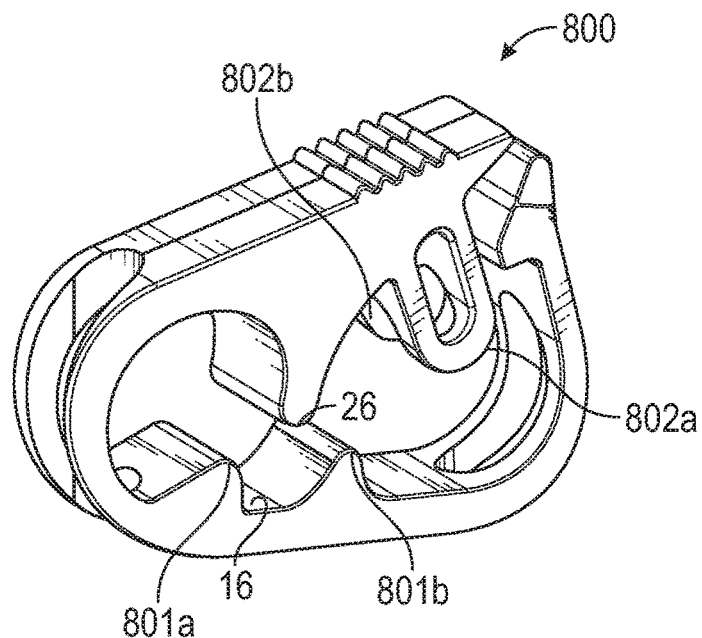
FIGS. 8A and 8B illustrate perspective side views of a pinch clamp having a clamping surface comprising raised and recessed surfaces in accordance with a representative embodiment of the present invention.
Figure 8B:
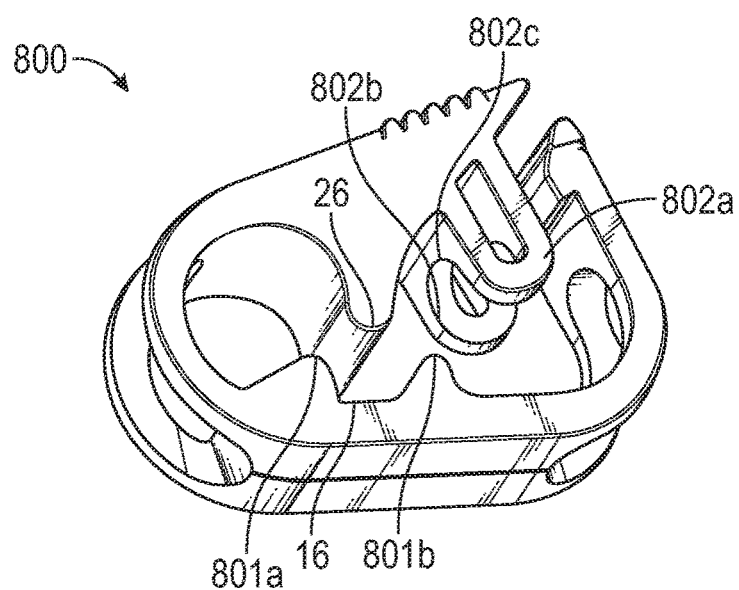

FIGS. 8A and 8B illustrate another embodiment of a pinch clamp 800 that is similar to pinch clamp 10. However, in pinch clamp 800, first clamping surface 16 is formed as a recessed surface positioned between raised surfaces 801a and 801b. Accordingly, when pinch clamp 800 is engaged, second clamping surface 26 inserts between raised surfaces 801a and 801b to contact first clamping surface 16. In this way, pinch clamp 800 provides multiple points of compression on the tubing. More specifically, raised surfaces 801a and 801b can provide compression on tubing in a distal and proximal direction respectively. This "arc" of compression can enhance the occlusion of the tubing to minimize the likelihood that the tubing will not be fully occluded when pinch clamp 800 is engaged. Also, due to the respective angles between second clamping surface 26 and raised surface 801b, a degree of positive displacement may occur as the tubing is occluded.

FIGS. 8A and 8B also show that pinch clamp 800 can include extensions 802a and 802b. In these figures, extensions 802a and 802b are shown as extending downwardly from the second arm. However, extensions 802a and 802b could equally extend upwardly from the first arm. In some embodiments, such as is shown in FIG. 8B, extensions 802a and 802b can include a rounded interconnect 802c. Rounded interconnect 802c can generally conform to the shape of tubing so that the tubing is securely contained between extensions 802a and 802b when pinch clamp 800 is engaged. This secure containment can function to inhibit the lateral movement between the first and second arms of pinch clamp 800. More particularly, contact between extension 802a or 802b and the tubing will resist lateral movement of the second arm with respect to the first arm so that second arm cannot easily be moved laterally to the point of disengaging from the first arm.

Figure 9:
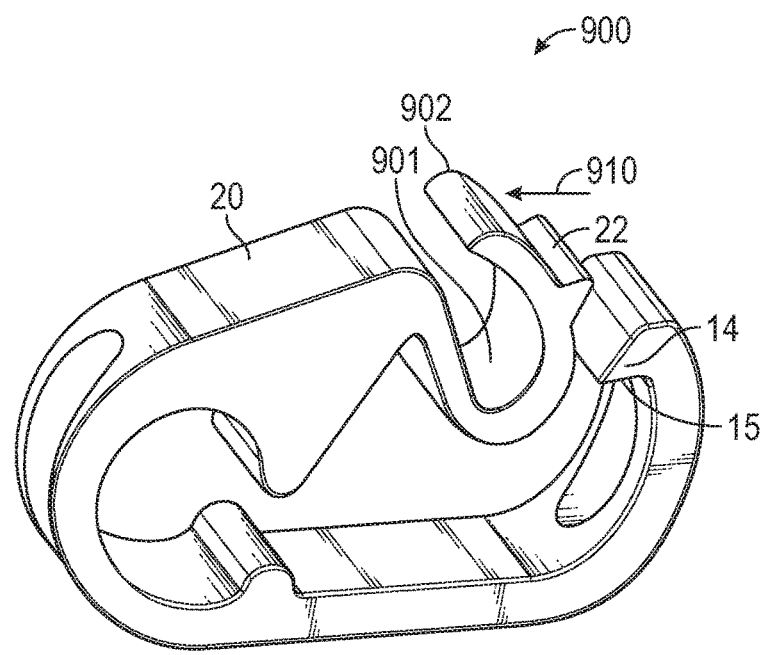
FIG. 9 illustrates a perspective side view of a pinch clamp having a terminal end configured to disengage the clamping surfaces by applying a force in a proximal direction in accordance with a representative embodiment of the present invention.

FIG. 9 illustrates an embodiment of a pinch clamp 900 that employs a different configuration for the terminal end of second arm 20. In contrast to the embodiments of pinch clamps described above, pinch clamp 900 is configured such that the second arm is disengaged from the first arm by applying a force against the second arm that is in a generally proximal direction 910.

As shown, second arm 20 includes a hinge 901 towards its distal end. A terminal end 902 of second arm 20 extends upwardly and proximally away from interface surface 22. As in previously-described embodiments, interface surface 22 inserts under ledge 15 to engage the pinch clamp. However, to disengage pinch clamp 900, a force in the proximal direction 910 can be applied to terminal end 902 rather than applying a force in a downward/distal direction on lip 14. Any of the other embodiments of pinch clamps described herein can alternatively be configured as shown in FIG. 9. Also, pinch clamp 900 can be configured to include any of the positive displacement features and/or a nesting component as described above.

Figure 10A:
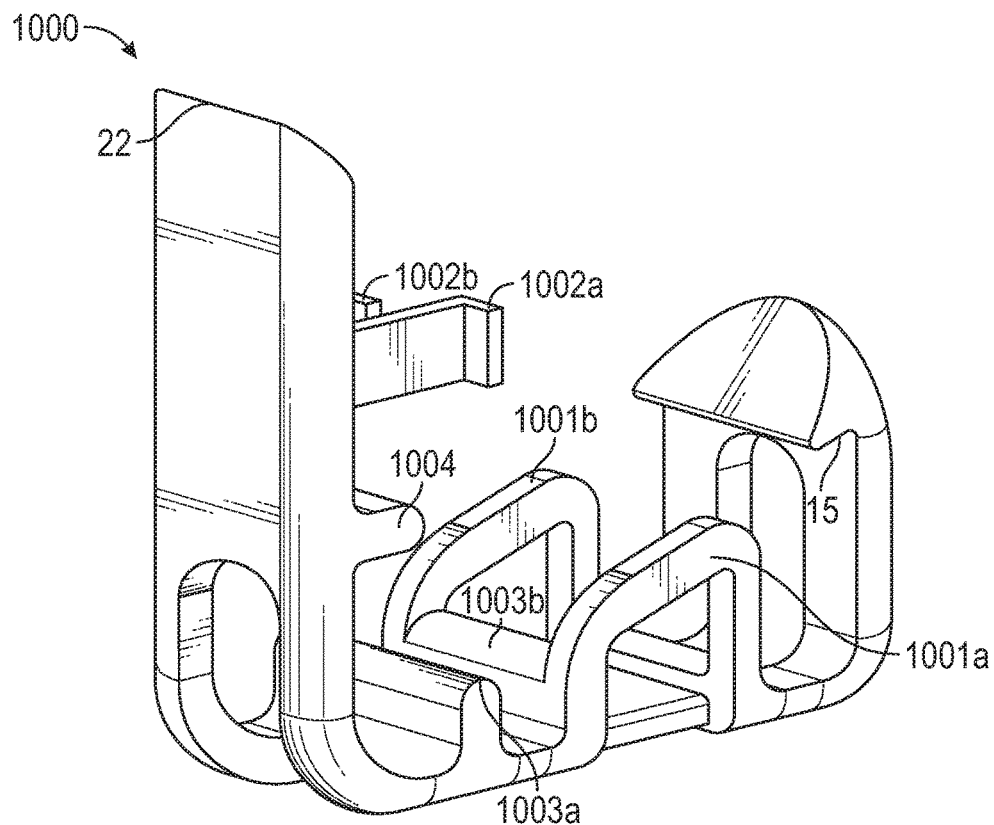
FIGS. 10A-10C illustrate various perspective side views of a pinch clamp having various retaining components in accordance with a representative embodiment of the present invention.
Figure 10B:
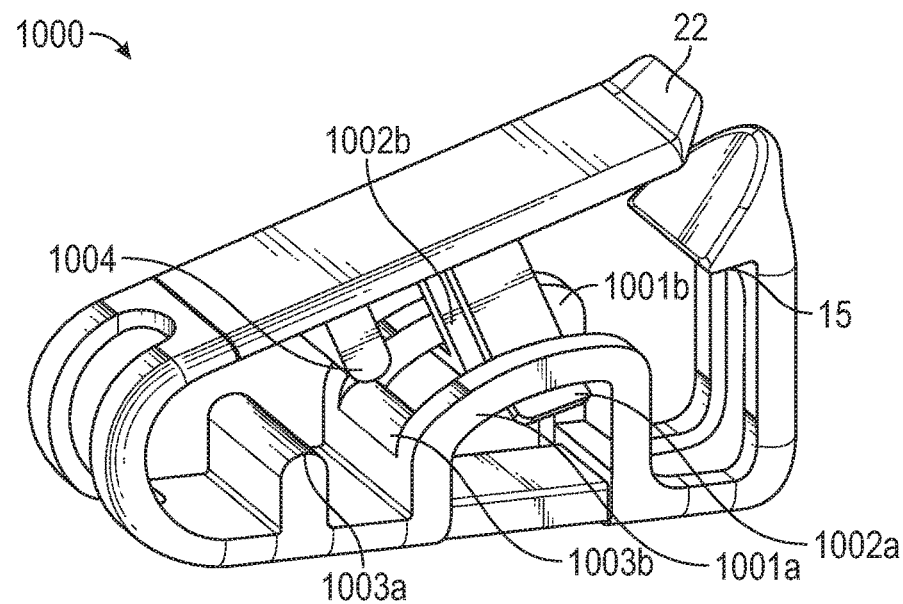
Figure 10C:
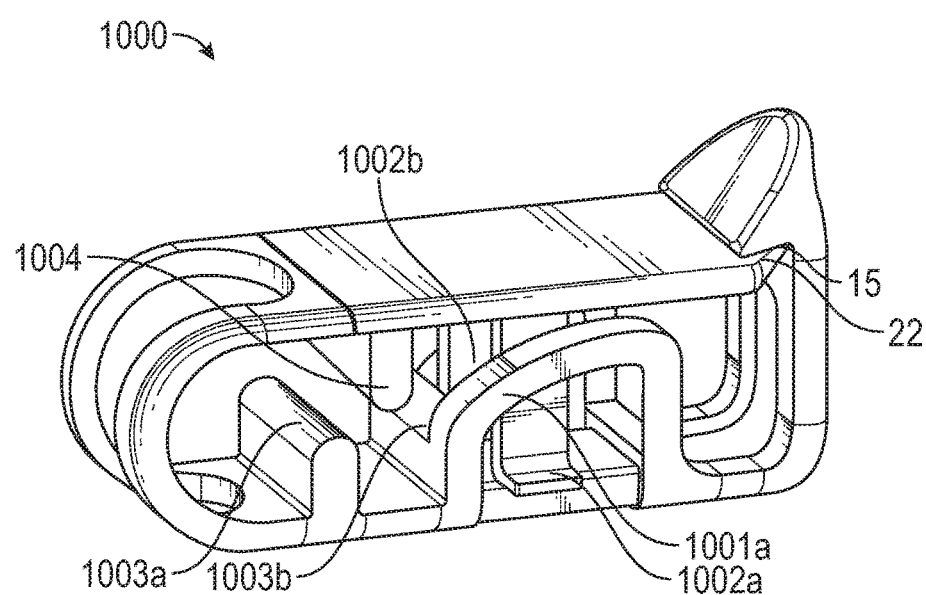

FIGS. 10A-10C illustrate another embodiment of a pinch clamp 1000. Pinch clamp 1000 includes protrusions 1003a and 1003b that extend upwardly from the first arm and protrusion 1004 that extends downwardly from the second arm. Protrusion 1004 can be configured to insert between protrusions 1003a and 1003b and therefore function to occlude the tubing in a similar manner as with pinch clamp 800. However, as best seen in FIG. 10C, in some embodiments, protrusion 1004 may have a length that is insufficient to cause protrusion 1004 to contact the first arm. In some embodiments, protrusions 1003a and 1003b may alternatively extend downwardly from the second arm while protrusion 1004 could extend upwardly from the first arm. Also, pinch clamp 1000 may equally be configured to include any of the other types of clamping surfaces described herein.

Pinch clamp 1000 may also include interlocking components that function both to limit the range of motion of the hinge between the first and second arm as well as to limit lateral movement between the first and second arm. These interlocking components include retaining components 1001a and 1001b and corresponding pivoting tabs 1002a and 1002b. As shown, retaining components 1001a and 1001b are positioned on opposite sides of pinch clamp 1000. Pivoting tabs 1002a and 1002b are also positioned on opposite sides of pinch clamp 1000 but are slightly inwardly offset with respect to retaining components 1001a and 1001b to allow each of pivoting tabs 1002a and 1002b to insert into an opening formed within the corresponding retaining component. Pivoting tabs 1002a and 1002b can each include an outwardly extending tip that interlocks with the retaining component once the pivoting tab has been inserted into the opening as is shown in FIG. 10B.

Pivoting tabs 1002a and 1002b can be configured to pivot inwardly to allow them to bypass retaining components 1001a and 1001b as they move from the position shown in FIG. 10A to the position shown in FIG. 10B. Once in the interlocked position shown in FIG. 10B, the outwardly extending tips of pivoting tabs 1002a and 1002b will retain the pivoting tabs in the interlocked position absent an inward force on the pivoting tabs. In other words, the interaction between the pivoting tabs and the retaining components limits the amount to which pinch clamp 1000 will open.

FIG. 10B represents the position of pinch clamp 1000 when in the disengaged state. To engage pinch clamp 1000, a downward force can be applied to the second arm to cause interface surface 22 to interlock with ledge 15 in a similar manner as described above with reference to pinch clamp 10. FIG. 10C represents the position of pinch clamp 1000 when in this engaged state. Upon disengaging interface surface 22 from ledge 15, pinch clamp 1000 can return to the disengaged state as shown in FIG. 10B. As indicated above, the interface between pivoting tabs 1002a and 1002b and retaining components 1001a and 1001b will then prevent pinch clamp 1000 from opening beyond this position.

The interface between pivoting tabs 1002a and 1002b and retaining components 1001a and 1001b will also inhibit lateral movement between the first and second arms. In this way, pinch clamp 1000 can be prevented from disengaging due to the second arm moving laterally to free interface 22 from ledge 15.

Figure 11:
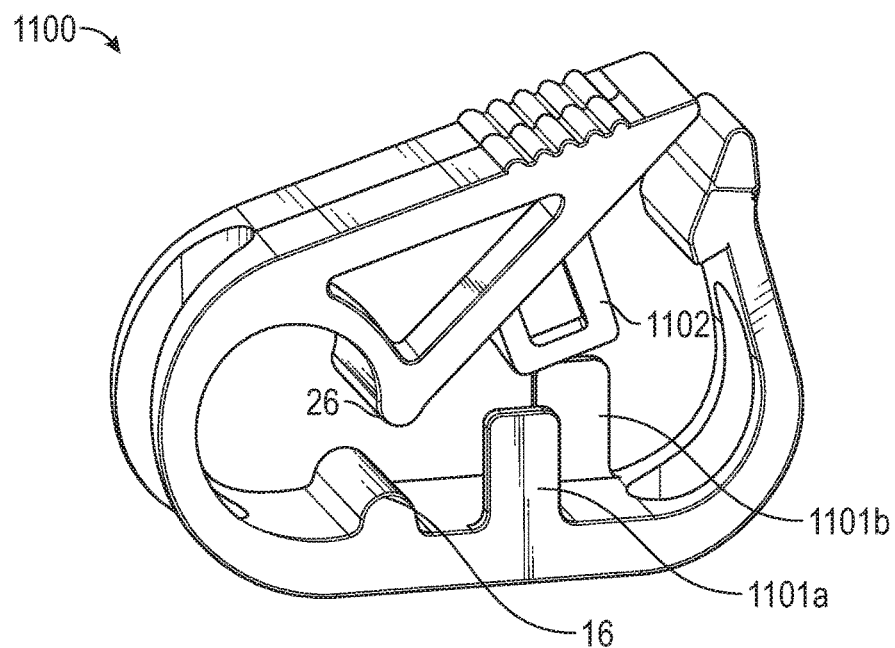
FIG. 11 illustrates a perspective side view of a pinch clamp having offset retaining components in accordance with a representative embodiment of the present invention.

FIG. 11 illustrates another embodiment of a pinch clamp 1100 that includes features for preventing the lateral disengagement of the pinch clamp. Pinch clamp 1100 includes extensions 1101a and 1101b which are similar to extensions 100 described above. In some embodiments, extensions 1101a and 1101b can be offset from one another as is shown in FIG. 11. Additionally, pinch clamp 1100 can include an inner extension 1102 that extends from an opposite arm from extensions 1101a and 1101b (which in the depicted example is from the second arm).

Inner extension 1102 can be positioned between extensions 1101a and 1101b such that inner extension 1102 would contact one or both of extensions 1101a and 1101b if the second arm were moved laterally with respect to the first arm. This interaction between extensions 1101a/1101b and inner extension 1102 can prevent the lateral disengagement of pinch clamp 1100. Inner extension 1102 can be configured with a length that forms a gap between inner extension 1102 and the first arm when pinch clamp 1100 is engaged. In some embodiments, this gap may be small enough to cause the tubing to be compressed. In such embodiments and due to the prior occlusion that would be caused by first and second clamping surfaces 16 and 26, inner extension 1102 can cause positive fluid displacement. Also, although not depicted, in some embodiments, inner extension 1102 can be configured to receive the tubing in a similar manner as rounded interconnect 802c. Pinch clamp 1100 may also include any of the other configurations of first and second clamping surfaces described herein.

Figure 12:
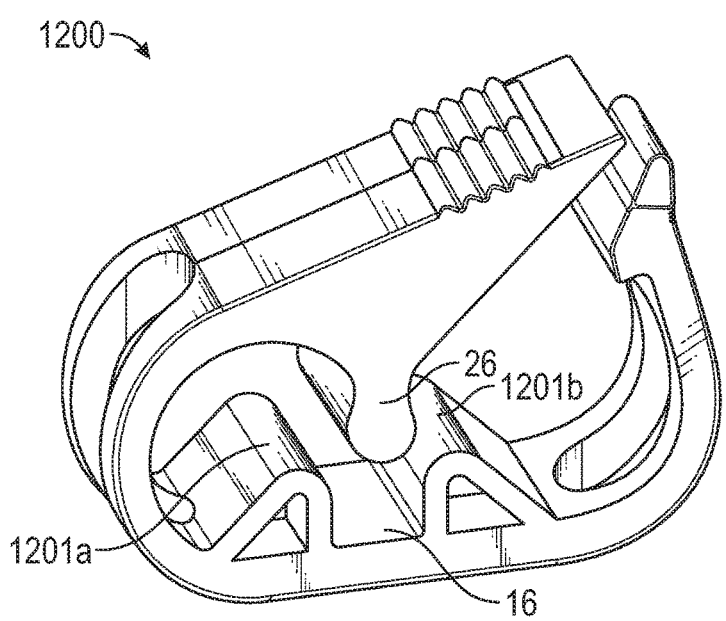
FIG. 12 illustrates a perspective side view of a pinch clamp having a clamping surface comprising raised and recessed surfaces in accordance with a representative embodiment of the present invention.

FIG. 12 illustrates another embodiment of a pinch clamp 1200. Pinch clamp 1200 is configured in a similar manner as pinch clamp 800 in that first clamping surface 16 is formed as a recessed surface positioned between raised surfaces 1201a and 1201b. Second clamping surface 26 can insert between raised surfaces 1201a and 1201b to provide an arc of compression along the tubing. Also, because second clamping surface 26 is positioned between raised surfaces 1201a and 1201b when pinch clamp 1200 is engaged, lateral disengagement can be prevented. More specifically, if the second arm is moved laterally with respect to the first arm, second clamping surface 26 will contact one or both of raised surfaces 1201a and 1201b to inhibit further lateral movement.

Figure 13A:
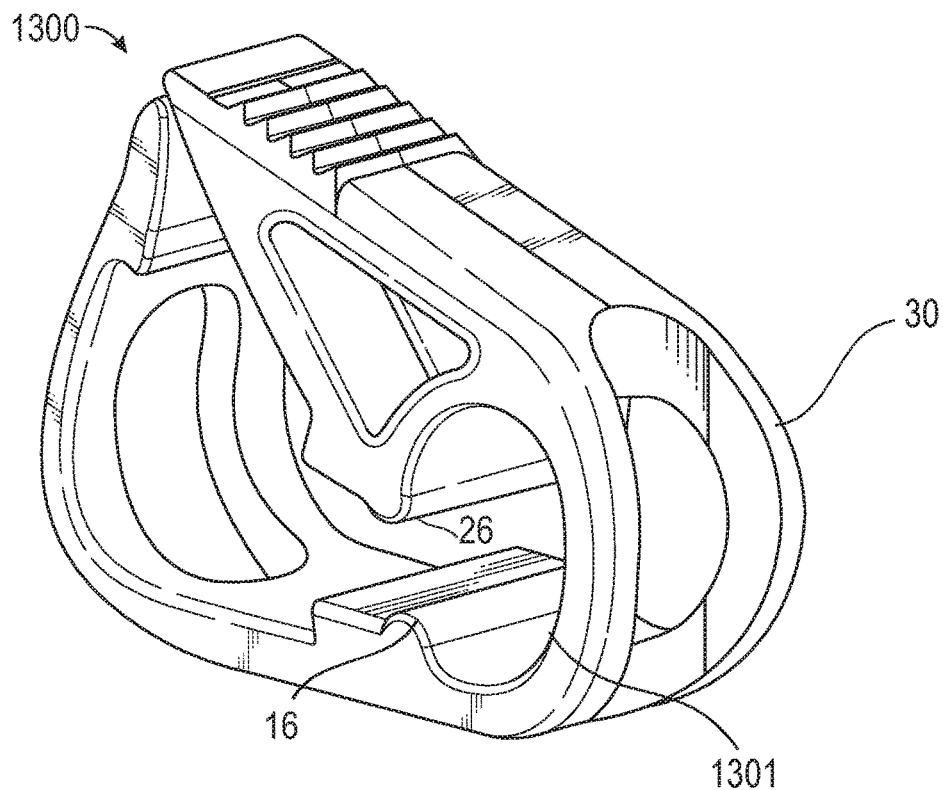
FIGS. 13A and 13B illustrate a perspective side view and a rear view respectively of a pinch clamp that has rounded edges and an elliptical-shaped hinge.
Figure 13B:
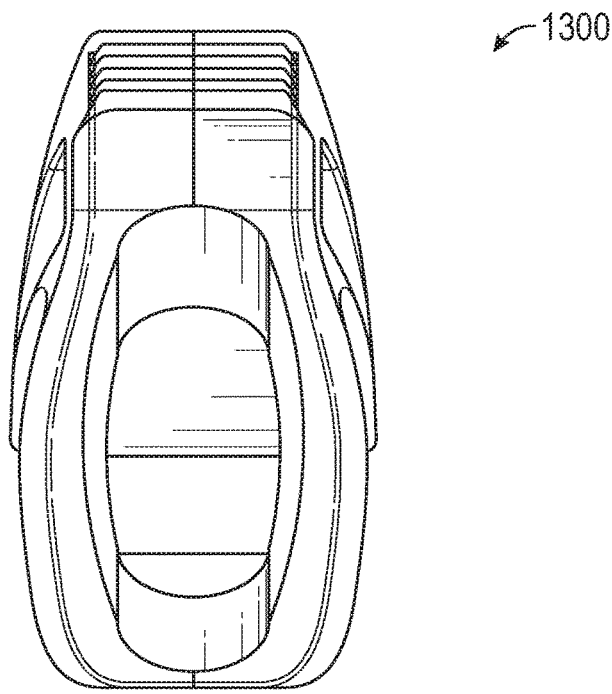

FIGS. 13A and 13B illustrate another embodiment of a pinch clamp 1300. Pinch clamp 1300 can include clamping surfaces 16 and 26 which can be configured in any of the various ways described above as well as a hinge 30. Hinge 30 can be structured to form an elliptical-shaped opening 1301 between hinge 30 and clamping surfaces 16 and 26. Additionally, as is best seen in FIG. 13B, pinch clamp 1300 can include rounded outer edges which can enhance patient comfort.

Figure 14A:
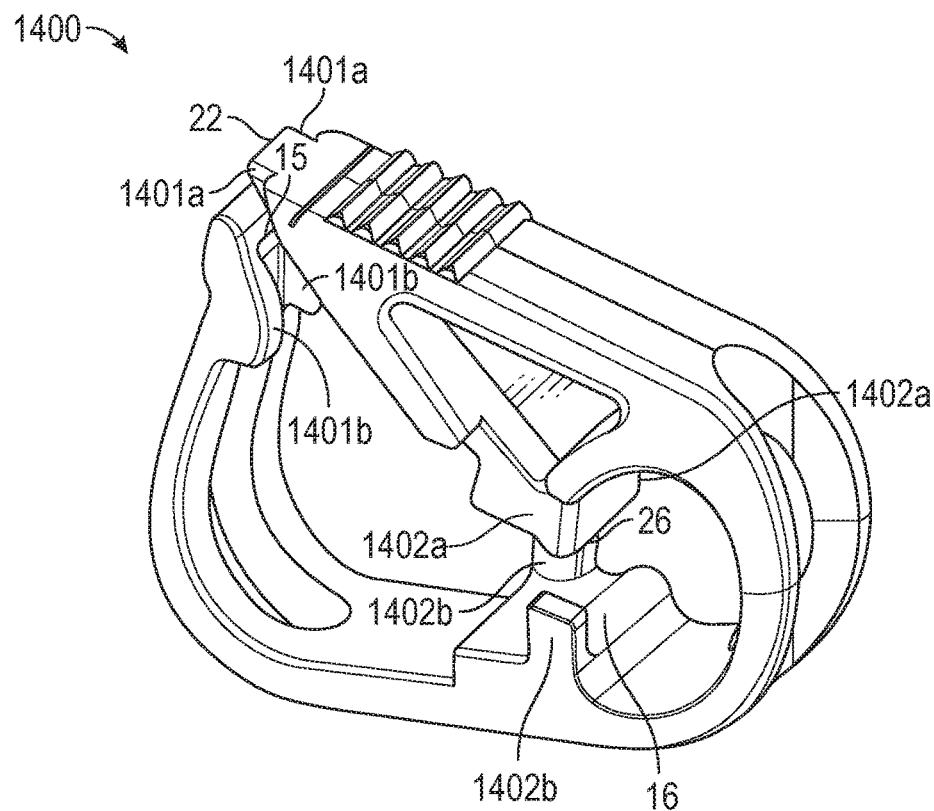
FIGS. 14A and 14B illustrate a perspective side view and a side view respectively of a pinch clamp that includes various lateral disengagement prevention features.
Figure 14B:
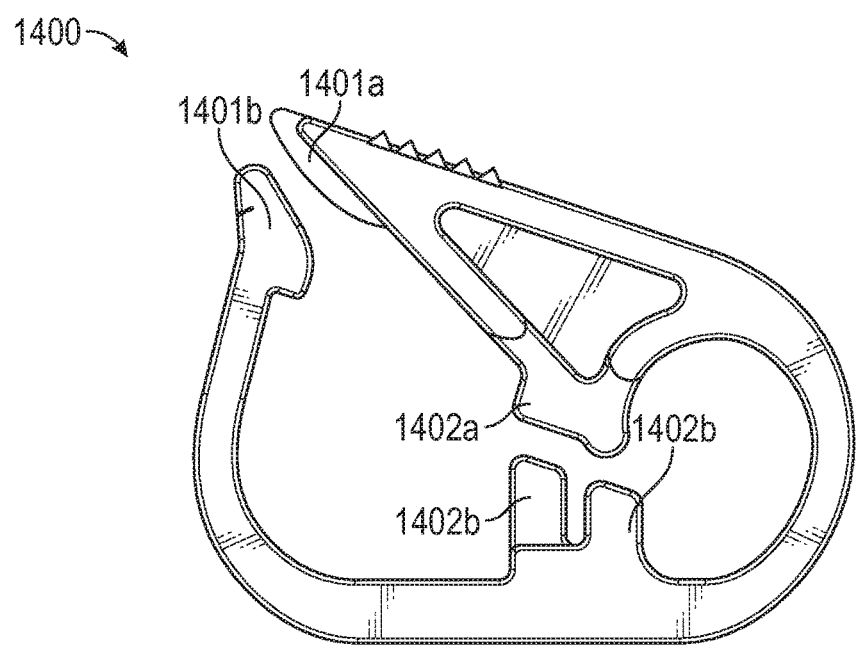

FIGS. 14A and 14B illustrate another embodiment of a pinch clamp 1400 that includes various lateral disengagement prevention features. As with previously described pinch clamps, pinch clamp 1400 can include clamping surfaces 16 and 26. Additionally, to prevent lateral disengagement, clamping surface 26 can include recessed surfaces 1402a while clamping surface 16 can include lateral posts 1402b. As shown, lateral posts 1402b can be formed on opposing sides of clamping surface 16. Recessed surfaces 1402a can be sufficiently recessed to allow clamping surface 26 to insert between lateral posts 1402b. With clamping surface 26 inserted between lateral posts 1402b, lateral movement of clamping surface 26 with respect to clamping surface 16 will be prevented as recessed surfaces 1402a contact lateral posts 1402b. In some embodiments, including the depicted embodiment, lateral posts 1402b are offset.

Pinch clamp 1400 may also include lateral disengagement prevention features formed at interface surface 22. For example, as shown in FIGS. 14A and 14B, interface surface 22 may be formed with outwardly facing recessed surfaces 1401a which can be positioned between inwardly facing lateral protrusions 1401b that are positioned on opposing sides of ledge 15. Accordingly, when interface surface 22 is secured under ledge 15, lateral protrusions 1401b will contact recessed surfaces 1401a to prevent lateral movement. Although pinch clamp 1400 is shown as including two types of lateral disengagement prevention features, in other embodiments, a pinch clamp may only include one of these features.

Figure 15:
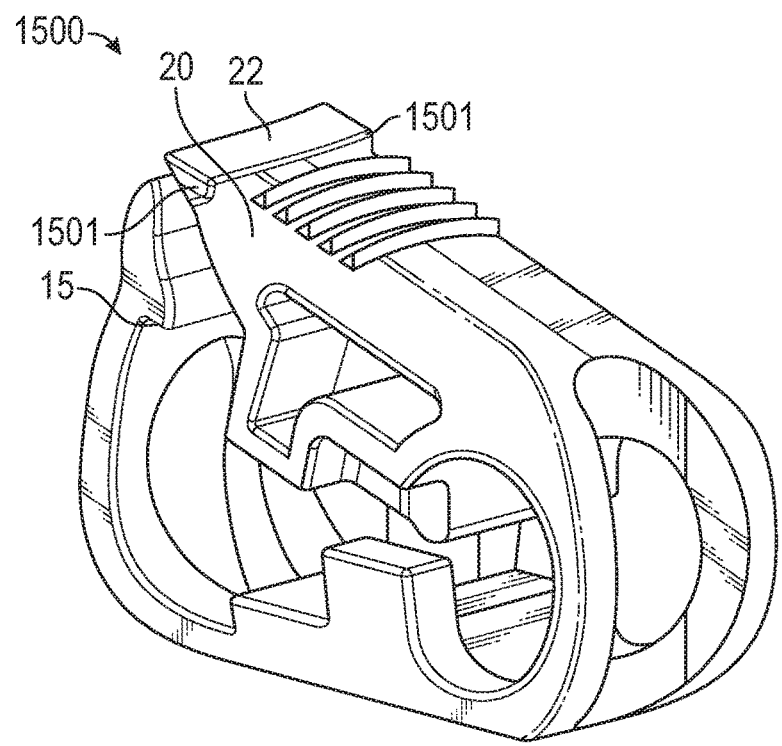
FIG. 15 illustrates a perspective side view of a pinch clamp that includes various lateral disengagement prevention features.

As shown in FIGS. 13A and 13B, various embodiments of a pinch clamp may include rounded outer edges. However, by rounding the outer edges, the width of interface surface 22 and ledge 15 may be reduced thereby increasing the likelihood that the pinch clamp may be laterally disengaged. To address such concerns, in some embodiments of pinch clamps that include rounded outer edges, particularly those that do not employ another type of lateral disengagement prevention feature, interface surface 22 can be molded or otherwise formed to include ends 1501 that protrude beyond the outer surface of the remaining portions of second arm 20, as shown in FIG. 15. These protruding ends 1501 increase the width of interface surface 22 to thereby maximize the amount of lateral displacement that would be required to disengage the pinch clamp. Also, in embodiments that employ protruding ends 1501, the clamping surfaces may also be configured to include lateral disengagement prevention features similar to those described above with reference to FIGS. 14A and 14B.

Figure 16A:
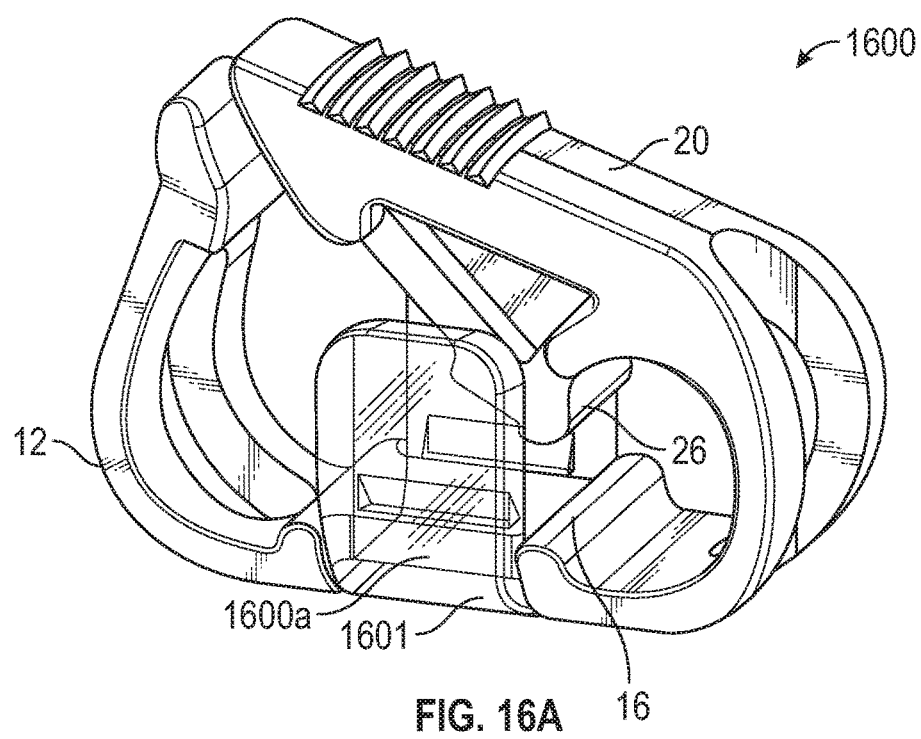
FIG. 16A illustrates a pinch clamp that employs a separate lateral disengagement prevention component.
Figure 16B:
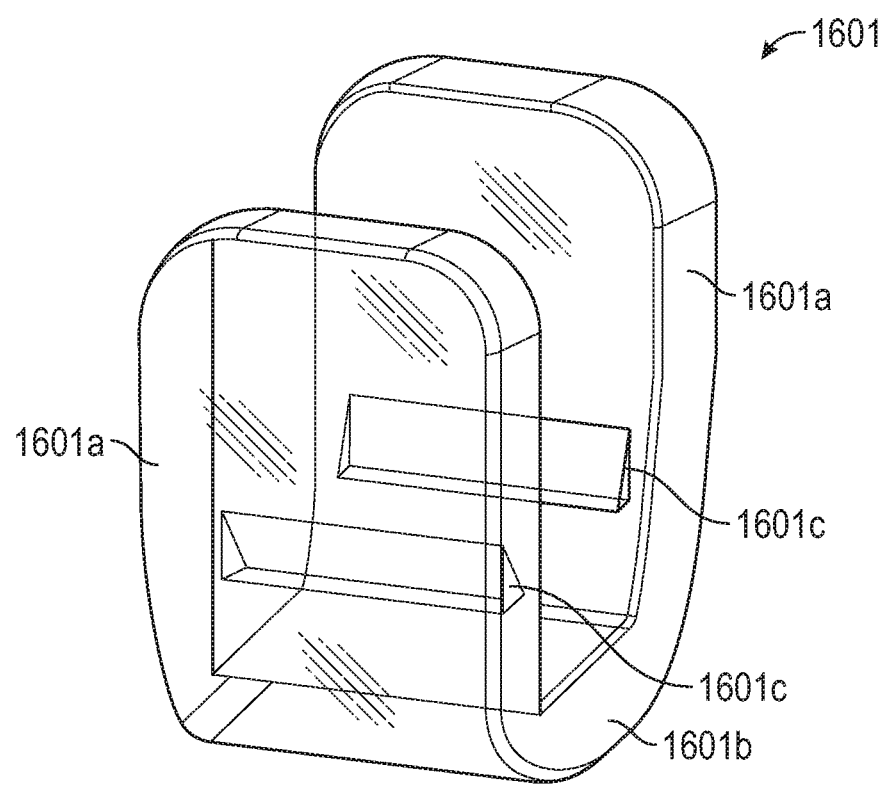
FIG. 16B illustrates the lateral disengagement prevention component of FIG. 16A in isolation.

FIG. 16A illustrates another embodiment of a pinch clamp 1600 that employs a separate component 1601 to prevent lateral disengagement while FIG. 16B shows component 1601 in isolation. As shown, pinch clamp 1600 can include a recessed section 1600a that is formed in first arm 12 and positioned generally below and to the side of clamping surface 16. Recessed section 1600a can be shaped and sized to accommodate lateral disengagement prevention component 1601 in a manner that causes the outer surfaces of lateral disengagement prevention component 1601 to substantially align with the outer surfaces of first arm 12. Therefore, even though a separate component is used, there will not be sharp edges or transitions between pinch clamp 1600 and component 1601.

Component 1601 can have a U-shape that is formed by a bottom section 1601b and opposing arms 1601a that extend upwardly from opposite ends of bottom section 1601b. Each of arms 1601a can include an inward protrusion 1601c that is positioned such that the bottom ledge of each protrusion 1601c is located on top of first arm 12 when bottom section 1601b is secured within recessed section 1600a. Protrusions 1601c therefore function to prevent component 1601 from being separated from pinch clamp 1600. In some embodiments, component 1601 may also be secured to arm 12 using an adhesive. Arms 1601a can have a sufficient length to ensure that they overlap second arm 20 or to at least overlap a portion of clamping surface 26 to thereby limit how far arm 20 can be laterally displaced relative to arm 12.

In addition to preventing lateral disengagement of the pinch clamp, the various lateral disengagement prevention features/components described herein also function to center the tubing within the pinch clamp to ensure proper clamping. Accordingly, embodiments of the present invention ensure that the tubing is properly clamped and will not unintentionally become disengaged.

Figure 17:
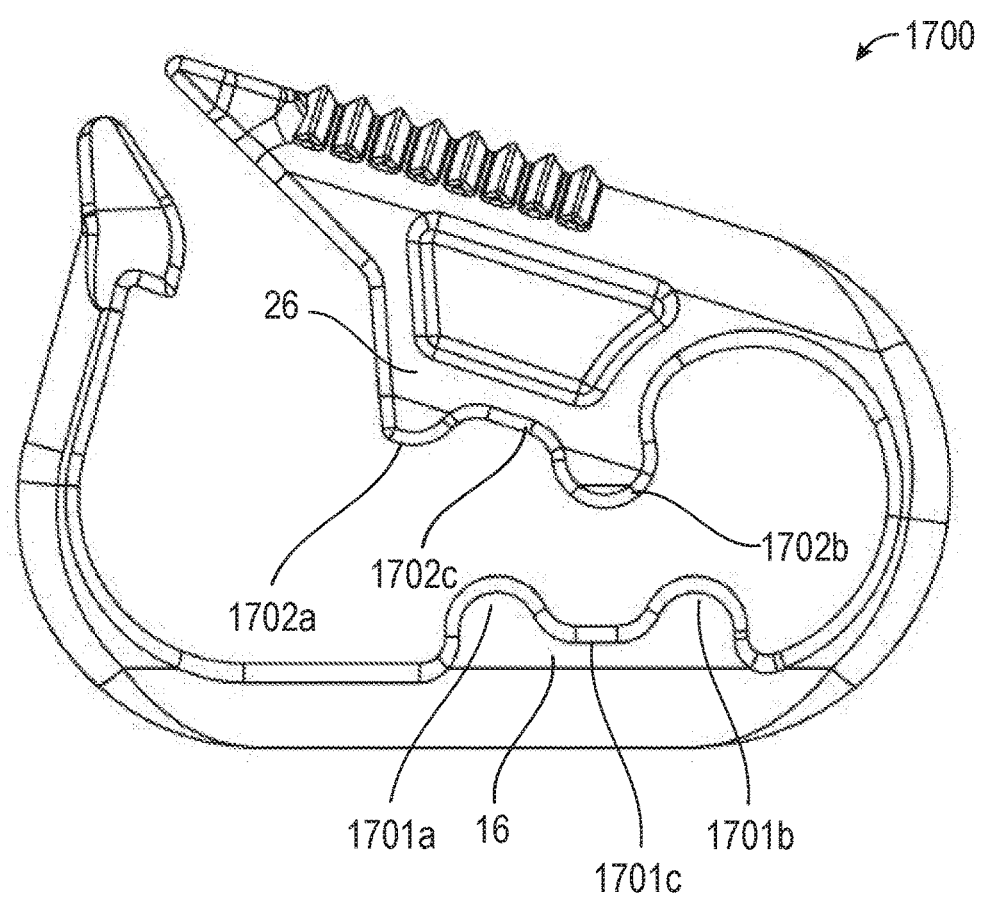
FIG. 17 illustrates a pinch clamp having clamping surfaces that are configured to provide positive fluid displacement.

FIG. 17 illustrates another embodiment of a pinch clamp 1700 in which clamping surfaces 16 and 26 are configured to provide positive fluid displacement. As shown, clamping surface 16 includes raised surfaces 1701a and 1701b which are spaced apart to form a recessed surface 1701c. Clamping surface 26 is similarly configured with raised surfaces 1702a and 1702b which are spaced apart to form a recessed surface 1702c. Raised surfaces 1702a and 1702b can be distally offset relative to raised surfaces 1701a and 1701b such that, when pinch clamp 1700 is engaged, raised surface 1702b will insert into recessed surface 1701c and raised surface 1701a will insert into recessed surface 1702c.

Additionally, raised surface 1702b can be vertically offset relative to recessed surface 1702c such that raised surface 1702b will insert into recessed surface 1701c prior to raised surface 1701a inserting into recessed surface 1702c. This vertical offset will cause tubing to first be clamped within recessed surface 1701c and then clamped within recessed surface 1702c. As a result, fluid contained within the portion of the tubing that is distal to raised surface 1702b (or with respect to the orientation shown in FIG. 17, to the left of raised surface 1702b) after raised surface 1702b is clamped will be forced distally (or towards the patient) when raised surface 1701a is subsequently clamped.

The inclusion of raised surfaces 1702a and 1701b increase the length of tubing that will be clamped. For example, as raised surface 1701a inserts into recessed surface 1702c, the tubing will be clamped along recessed surface 1702c and raised surface 1702a. Raised surface 1702a can also be vertically offset with respect to recessed surface 1702c so that raised surface 1702a clamps the tubing after raised surface 1701a thereby increasing the amount of positive fluid displacement. In FIG. 17, this vertical offset is accomplished by angling clamping surface 26 relative to clamping surface 16 so that the distance between the two surfaces increases from the proximal to the distal ends of the surfaces. However, the vertical offset could also be accomplished in other ways such as by angling clamping surface 16. This configuration of clamping surfaces 16 and 26 can be employed in conjunction with any of the above described lateral displacement features.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A pinch clamp device, comprising:
    a first arm, comprising a first end, a second end, wherein the first end of the first arm comprises a lip and the second end of the first arm comprises a first clamping surface;
    a second arm, comprising a first end and a second end, wherein the first end of the second arm comprises a terminal end and the second end of the second arm comprises a second clamping surface positioned opposite the first clamping surface;
    a hinge interconnecting the second end of the first arm and the second end of the second arm;
    a first side surface and a second side surface, wherein the first side surface and the second side surface extend between the lip and the terminal end, wherein the first clamping surface and the second clamping surface extend in between the first side surface and the second side surface,
wherein the second clamping surface comprises a first end and a second end, wherein the first end of the second clamping surface is closer to the hinge and the first clamping surface than the second end of the second clamping surface, wherein the first end of the second clamping surface comprises a first material, wherein the second end of the second clamping surface comprises a second material, wherein the second material is less rigid than the first material and does not extend to the first end of the second clamping surface.

2. The pinch clamp device of claim 1, further comprising:
a nesting component comprising opposing sidewalls coupled together via an interconnect, the interconnect being sized to fit inside of the hinge and to position the opposing sidewalls outside and adjacent to the first arm and the second arm.

3. The pinch clamp device of claim 2, wherein the nesting component further includes a raised feature on an interior surface of one or more of the opposing sidewalls and disposed between the first arm and the second arm, the raised feature contacting one or both of the first arm and the second arm to limit rotation of the nesting component.

4. The pinch clamp device of claim 1, wherein one or both of the first clamping surface and the second clamping surface is formed as a recessed surface between raised surfaces.

5. The pinch clamp device of claim 4, further comprising:
extensions that extend from opposing sides of one of the first arm or the second arm.

6. The pinch clamp device of claim 5, wherein the extensions are coupled together via a rounded interconnect, the rounded interconnect forming an opening through which tubing passes between the extensions.

7. The pinch clamp device of claim 1, wherein the first end of the second arm includes a second hinge.

8. The pinch clamp device of claim 7, wherein the second hinge allows the terminal end of the second arm to pivot towards the hinge that interconnects the first and second arm.

9. The pinch clamp device of claim 1, wherein one of the first arm or the second arm includes retaining components and the other of the first arm or the second arm includes pivoting tabs which interlock with the retaining components to limit the extent to which the hinge opens.

10. The pinch clamp device of claim 9, wherein the retaining components are positioned on opposing sides of the first arm or the second arm and the pivoting tabs are inwardly offset with respect to the retaining components.

11. The pinch clamp device of claim 1, wherein one of the first arm or the second arm includes extensions positioned on opposing sides of the first arm or the second arm and the other of the first arm or the second arm includes an inner extension that inserts between the opposing extensions when the pinch clap device is engaged.

12. The pinch clamp device of claim 1, wherein the first arm includes raised surfaces positioned on each side of the first clamping surface, the second clamping surface inserting between the raised surfaces when the pinch clamp device is engaged.

13. The pinch clamp device of claim 1, wherein the hinge forms an elliptical-shaped opening between the hinge and the first clamping surface and the second clamping surface.

14. The pinch clamp device of claim 1, wherein outer edges of the first arm and the second arm are rounded.

15. The pinch clamp device of claim 14, the terminal end of the second arm forms an interface surface having ends that protrude outwardly beyond the outer edges of the second arm.

16. The pinch clamp device of claim 1, wherein one of the first clamping surface or the second clamping surface includes lateral posts and the other of the first clamping surface or the second clamping surface includes recessed surfaces that are positioned between the lateral posts when the first clamping surface and the second clamping surface are engaged.

17. The pinch clamp device of claim 1, wherein the terminal end of the second arm forms an interface surface that includes outwardly facing recessed surfaces and the first arm includes inwardly facing lateral protrusions between which the recessed surfaces are positioned when the interface surface is secured under a ledge formed by the lip.

18. The pinch clamp device of claim 1, wherein the first arm includes a recessed section positioned below the first clamping surface, the pinch clamp device further comprising:
a lateral disengagement prevention component having a bottom section and two opposing arms that extend upwardly from opposite ends of the bottom section;
wherein the recessed section is configured to accommodate the lateral disengagement prevention component such that the opposing arms are positioned overtop the second arm.

19. The pinch clamp device of claim 18, wherein each of the opposing arms includes an inward protrusion that extends from an inner surface of the arm, the inward protrusion being positioned such that a bottom surface of the inward protrusion contacts a top surface of the first arm when the bottom section of the lateral disengagement prevention component is positioned within the recessed section.

20. The pinch clamp device of claim 1, wherein the first clamping surface comprises a first end and a second end, wherein the first end of the first clamping surface is closer to the hinge and the first clamping surface than the second end of the first clamping surface, wherein the first end of the first clamping surface comprises the first material, wherein the second end of the first clamping surface comprises the second material, wherein the second material is less rigid than the first material and does not extend to the first end of the first clamping surface, wherein the first clamping surface is generally planar, wherein the first end of the first clamping surface and the first end of the second clamping surface are configured to contact opposing portions of a tubing extending through the pinch clamp device.

\* \* \* \* \*